United States Patent
Tuskan et al.

(10) Patent No.: US 10,167,523 B2
(45) Date of Patent: Jan. 1, 2019

(54) GENE IMPACTING BIOMASS FORMATION AND RECALCITRANCE AND METHODS OF USE

(71) Applicant: UT-Battelle, LLC, Oak Ridge, TN (US)

(72) Inventors: Gerald A. Tuskan, Oak Ridge, TN (US); Udaya C. Kalluri, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 146 days.

(21) Appl. No.: 15/145,996

(22) Filed: May 4, 2016

(65) Prior Publication Data

US 2016/0326602 A1 Nov. 10, 2016

Related U.S. Application Data

(60) Provisional application No. 62/157,038, filed on May 5, 2015.

(51) Int. Cl.
| | |
|---|---|
| *C12N 15/82* | (2006.01) |
| *C12Q 1/6895* | (2018.01) |
| *C07K 14/415* | (2006.01) |

(52) U.S. Cl.
CPC .......... *C12Q 1/6895* (2013.01); *C07K 14/415* (2013.01); *C12N 15/8218* (2013.01); *C12N 15/8261* (2013.01); *C12Q 2600/13* (2013.01); *C12Q 2600/156* (2013.01); *C12Q 2600/158* (2013.01); *Y02A 40/146* (2018.01)

(58) Field of Classification Search
None
See application file for complete search history.

(56) References Cited

U.S. PATENT DOCUMENTS

2013/0333061 A1* 12/2013 Wu ..................... C07K 14/415
800/260

OTHER PUBLICATIONS

Tuskan et al., NCBI, GenBank Sequence Accession No. EEE83709.1; Published Oct. 18, 2013.*

Anne Endler et al., "Cellulose Synthases and Synthesis in Arabidopsis," Molecular Plant, 2011, pp. 199-211, vol. 4, No. 2.
Chunxiang Fu et al., "Genetic Manipulation of Lignin Reduces Recalcitrance and Improves Ethanol Production from Switchgrass," PNAS, 2011, pp. 3803-3808, vol. 108, No. 9.
Udaya C. Kalluri et al., "Systems and Synthetic Biology Approaches to Alter Plant Cell Walls and Reduce Biomass Recalcitrance," Plant Biotechnology Journal, 2014, pp. 1207-1216, vol. 12.
Eshchar Mizrachi et al., "Cellulose Factories: Advancing Bioenergy Production from Forest Trees," New Phytologist, 2012, pp. 54-62, vol. 194.
Evandro Novaes, et al., "Quantitative Genetic Analysis of Biomass and Wood Chemistry of Populus Under Different Nitrogen Levels," New Phytologist, 2009, pp. 878-890, vol. 182.
Blake A Simmons, et al., "Advances in Modifying Lignin for Enhanced Biofuel Production," Plant Biology, 2010, pp. 313-320, vol. 13.
Gancho T. Slavov, et al., "Genome Resequencing Reveals Multiscale Geographic Structure and Extensive Linkage Disequilibrium in the Forest Tree Populus Trichocarpa," New Phytologist, 2012, pp. 713-725, vol. 196.
Michael H. Studer, et al., "Lignin Content in Natural Populus Variants Affects Sugar Release," PNAS, 2011, pp. 6300-6305, vol. 108, No. 15.
Wilfred Vermerris, et al., Molecular Breeding to Enhance Ethanol Production from Corn and Sorghum Stover, Crop Sci., 2007, pp. S142-S153, vol. 47, No. S3.
Jill L. Wegrzyn, et al., "Association Genetics of Traits Controlling Lignin and Cellulose Biosynthesis in Black Cottonwood (Populus Trichocarpa, Salicaceae) Secondary Xylem," New Phytologist, 2010, pp. 515-532, vol. 188.
Tongming Yin, et al., "Differential Detection of Genetic Loci Underlying Stem and Root Lignin Content in Populus," PLoS One, 2010, p. e14021, vol. 5, Issue 11.

* cited by examiner

*Primary Examiner* — Vinod Kumar
(74) *Attorney, Agent, or Firm* — Edna I. Gergel

(57) ABSTRACT

The invention provides plants having improved biomass properties of increased biomass quantity and density, increased cellulose content and deceased lignin content and improved sugar release efficiency, methods of generating (genetically modifying) and/or selecting (natural variant collections) plants with such preferred attributes of cellulose, lignin and sugar release, and uses of such plants. The inventors have determined that the expression of the gene, Potri.001G375700 (belonging to IQD signaling protein family containing a canonical calmodulin-binding domain) and/or activity of Potri.001G375700, modulates cellulose, lignin synthesis, sugar release and growth in plants.

4 Claims, 11 Drawing Sheets

Specification includes a Sequence Listing.

SEQUENCE LISTING

```
<160> NUMBER OF SEQ ID NOS: 3

<210> SEQ ID NO 1
<211> LENGTH: 1967
<212> TYPE: DNA
<213> ORGANISM: Populus trichocarpa

<400> SEQUENCE: 1
cccctttcca cctatttctt gcattgcact tcaccttcta cttcttaatt aatacttgga      60
gtcccaatat tgatctccac aacccaatcc aacgaagaat gtgttgcttc tctctttgaa     120
cccccaataa aaacaaacat gggttgtctc ttctctggga actggttgaa gtcaattata     180
agaacgagaa aggcgaagaa agatgcatca aagaaagtaa aggtacactc ggctaccgaa     240
```

-continued

```
aaggcaaacg ggtcaaagga gagctcaccc gcccatggag aatcaagtaa tcttgccaat    300
ggtgatttgg agagcaatat tcatgttgct cctggattgt ctgctgaata tatagctgct    360
gtcaggattc aagatgcttt tcgggcatac aaggcaagaa agcaatgca ccgtcttaag    420
ggcgccgtga ggttcaatgt gctgattcat ggtcatgaca ctcaaaagca agcttcaagc    480
acattaagcc atattcattc atggagcaac atacaggcac agattagagc cgccggcac    540
catatggtca ccgaaggccg tatcaagcaa aagaaattag aaaaccagtt gaaactcgag    600
gccagacttc aagagattga ggtggagtgg tgcggtggct ccgataccat ggaggaaatc    660
cttttccagga tccagcaaag agaagaagca gcagtaaagc gtgaacgagc catggcatat    720
gccttctctc atcagtggag agccaaccct acccaatatc taggccaggc ctattacagc    780
cttggcaaag aaaactgggg ttggagctgg aaggagcgct ggattgctgc tcggccatgg    840
gagattaggg ttcatgctga gcttcataac ctcaagaaag ctcatccaaa gcaagagagc    900
aaaacgacac ttccaaccaa acctgctttg tcaaatggga aggtgactgc taaatctaaa    960
atgttgccta gcccagctgt ggattgtcaa gctgcccagg ttgccagttc tacagccggc   1020
tcgtctcatc tgctgattcc aagttgacct tcgtgatgct cccttcttga tcctgtgtct   1080
ctgtattgtt tattttcggg gttggtgtga gattggcatg cagcgtgtaa aataaacata   1140
ttttttgctta cagttattat taagtaaatt atcttagtaa ctaaaaagat tcatcgagca   1200
aatttggctt gttcggtaat gacaagaggc ttcattttct tgcctcgaaa agaagtaaca   1260
tgggcatgga gctcgaaacc accgaggaag gatgcatttt aaccgtgaaa ttaattaatg   1320
ttcttaaatc agcaggcaac tagaagacct tcgcactttg agctagctcc tgtgttcatt   1380
atgcatcaat taccacacca atccattgtt agttgtatag ctagacaaga acaagtacat   1440
cccaacaaga tcttgcattc ctaaccccaa taaatcagta ttttttcttgt aaatcttagt   1500
ttactaaggc gctattcagc atgttcatct catgcgtacc ggtatccacc ccagccaccc   1560
tatgttatta gctttcaacg aggtaaaaga agggaatttg gtgtagaatt acgcttatgg   1620
ctgtaccttg cctttgcagt agtaattatc aactccagta taagaacac tagctagtaa   1680
ccagcagaaa gcaaaatgtc accatctcca ttgaatccaa gtgtttcact ttaatatatt   1740
ttggtttttc cccgggtgcc aaaaaaaaaa cccagctagg ctgaagagat tttttgagg   1800
gactgagatt tacagggtag gggaccgaag acagatggca aagtatcgca ttttagtgg   1860
tatccatctg tgtattcttc cataattgtg ccttgctgtg ttcatgccat tatgtgtatt   1920
cttccataat tgagctttgc tgtgttcatc ccattattta atagtgt                  1967
```

<210> SEQ ID NO 2
<211> LENGTH: 302
<212> TYPE: PRT
<213> ORGANISM: Populus trichocarpa

<400> SEQUENCE: 2

```
Met Gly Cys Leu Phe Ser Gly Asn Trp Leu Lys Ser Ile Ile Arg Thr
1               5                   10                  15

Arg Lys Ala Lys Lys Asp Ala Ser Lys Lys Val Lys Val His Ser Ala
            20                  25                  30

Thr Glu Lys Ala Asn Gly Ser Lys Glu Ser Ser Pro Ala His Gly Glu
        35                  40                  45

Ser Ser Asn Leu Ala Asn Gly Asp Leu Glu Ser Asn Ile His Val Ala
    50                  55                  60
```

```
Pro Gly Leu Ser Ala Glu Tyr Ile Ala Ala Val Arg Ile Gln Asp Ala
 65                  70                  75                  80

Phe Arg Ala Tyr Lys Ala Arg Lys Ala Met His Arg Leu Lys Gly Ala
                 85                  90                  95

Val Arg Phe Asn Val Leu Ile His Gly His Asp Thr Gln Lys Gln Ala
            100                 105                 110

Ser Ser Thr Leu Ser His Ile His Ser Trp Ser Asn Ile Gln Ala Gln
            115                 120                 125

Ile Arg Ala Arg Arg His His Met Val Thr Glu Gly Arg Ile Lys Gln
        130                 135                 140

Lys Lys Leu Glu Asn Gln Leu Lys Leu Glu Ala Arg Leu Gln Glu Ile
145                 150                 155                 160

Glu Val Glu Trp Cys Gly Gly Ser Asp Thr Met Glu Glu Ile Leu Ser
                165                 170                 175

Arg Ile Gln Gln Arg Glu Glu Ala Ala Val Lys Arg Glu Arg Ala Met
            180                 185                 190

Ala Tyr Ala Phe Ser His Gln Trp Arg Ala Asn Pro Thr Gln Tyr Leu
        195                 200                 205

Gly Gln Ala Tyr Tyr Ser Leu Gly Lys Glu Asn Trp Gly Trp Ser Trp
    210                 215                 220

Lys Glu Arg Trp Ile Ala Ala Arg Pro Trp Glu Ile Arg Val His Ala
225                 230                 235                 240

Glu Leu His Asn Leu Lys Lys Ala His Pro Lys Gln Glu Ser Lys Thr
                245                 250                 255

Thr Leu Pro Thr Lys Pro Ala Leu Ser Asn Gly Lys Val Thr Ala Lys
            260                 265                 270

Ser Lys Met Leu Pro Ser Pro Ala Val Asp Cys Gln Ala Ala Gln Val
        275                 280                 285

Ala Ser Ser Thr Ala Gly Ser Ser His Leu Leu Ile Pro Ser
    290                 295                 300
```

<210> SEQ ID NO 3
<211> LENGTH: 910
<212> TYPE: DNA
<213> ORGANISM: Populus trichocarpa

<400> SEQUENCE: 3

| | | | | | |
|---|---|---|---|---|---|
| catgggttgt | ctcttctctg | ggaactggtt | gaagtcaatt | ataagaacga | gaaaggcgaa | 60 |
| gaaagatgca | tcaaagaaag | taaaggtaca | ctcggctacc | gaaaaggcaa | acgggtcaaa | 120 |
| ggagagctca | cccgcccatg | gagaatcaag | taatcttgcc | aatggtgatt | tggagagcaa | 180 |
| tattcatgtt | gctcctggat | tgtctgctga | atatatagct | gctgtcagga | ttcaagatgc | 240 |
| ttttcgggca | tacaaggcaa | gaaagcaat | gcaccgtctt | aagggcgccg | tgaggttcaa | 300 |
| tgtgctgatt | catggtcatg | acactcaaaa | gcaagcttca | agcacattaa | gccatattca | 360 |
| ttcatggagc | aacatacagg | cacagattag | agcccgccgg | caccatatgg | tcaccgaagg | 420 |
| ccgtatcaag | caaaagaaat | tagaaaacca | gttgaaactc | gaggccagac | ttcaagagat | 480 |
| tgaggtggag | tggtgcggtg | gctccgatac | catggaggaa | atccttttcca | ggatccagca | 540 |
| aagagaagaa | gcagcagtaa | agcgtgaacg | agccatggca | tatgccttct | ctcatcagtg | 600 |
| gagagccaac | cctacccaat | atctaggcca | ggcctattac | agccttggca | agaaaactg | 660 |
| gggttggagc | tggaaggagc | gctggattgc | tgctcggcca | tgggagatta | gggttcatgc | 720 |
| tgagcttcat | aacctcaaga | aagctcatcc | aaagcaagag | agcaaaacga | cacttccaac | 780 |

```
caaacctgct ttgtcaaatg ggaaggtgac tgctaaatct aaaatgttgc ctagcccagc    840
tgtggattgt caagctgccc aggttgccag ttctacagcc ggctcgtctc atctgctgat    900
tccaagttga                                                           910
```

GENE IMPACTING BIOMASS FORMATION AND RECALCITRANCE AND METHODS OF USE

RELATED APPLICATIONS

This application asserts the priority of U.S. Provisional Application Ser. No. 62/157,038 filed on May 5, 2015, the contents of which are incorporated herein by reference.

STATEMENT REGARDING FEDERALLY SPONSORED RESEARCH

The United States Government has rights in this invention pursuant to contract no. DE-AC05-00OR22725 between the United States Department of Energy and UT-Battelle, LLC. The government has certain rights in this invention.

FIELD OF THE INVENTION

The invention relates to the field of plant genes. In particular, the invention relates to a gene involved in efficient cellulosic ethanol production.

BACKGROUND OF THE INVENTION

Production of renewable fuel from lignocellulosic plant biomass is based on extraction of cellulosic sugars from plant cell wall material. The percentage of usable substrate (cellulose content) in plant biomass and the ease of its extraction for ethanol conversion purposes are of prime importance in efforts to improve process and cost efficiency of bioethanol production. The ease of extractability of sugar substrates is hampered by plant "recalcitrance", a term referring to the inherent resistance of plant material to release polysaccharides and other desirable biomaterials from an interwoven matrix of desirable and undesirable materials (Lynd L R. et al., Science 251:1318-1323 (1991)). Extensive thermochemical and enzymatic treatment are needed to overcome this innate recalcitrance of plant stem biomass. Lignin content, its crosslinkages with wall carbohydrates and cell wall architecture are some known causes of recalcitrance. Furthermore, lignin processing creates inhibitory byproducts, such as phenolic and acetylated compounds, that hamper further extraction and fermentation. Phenolics and acetyl esters released during treatment of cell wall polymers can inhibit saccharification of biomass. The released acetate is also inhibitory to the organisms used to ferment the sugars into useful byproducts. Overcoming plant recalcitrance to releasing biomaterials bound in the cell wall as well as increasing the content of desirable substrates (cellulose) are therefore issues of primary importance in the development of biofuel technology.

Cellulose, composed of unbranched chains of beta-1-4 linked D-glucose units, is the most abundant biopolymer on earth and the key substrate for bioethanol production from lignocellulosic biomass. It is suggested in literature that factors such as (i) composition, number and arrangement of CESA (catalytic cellulose biosynthesis enzyme)—containing functional complexes, or rosette complexes and wall associated (KORRIGAN, KOBITO, COBRA) membrane associated (CSI) and soluble proteins (SuSy) influence the cellulose biosynthesis pathway (Endler and Persson, Arabidopsis. Mol. Plant. 2011; 4:199-211; Mizrachi et al., New Phytol. 2012; 194:54-62). Discovery of regulatory and signaling factors critical to determination of the cellulose properties (content, degree of polymerization and crystallinity) of plant cell walls and biomass are an important consideration in biomass improvement strategies (Kalluri et al. 2014, Plant Biotechnol J. 2014 December; 12(9):1207-16. doi: 10.1111/pbi.12283. Epub 2014 Nov. 3).

Lignins, complex interlinking biopolymers derived from hydroxyphenylpropanoids, provide rigidity and structure to plant cell walls for plant growth and transport of water and nutrients, and are significant contributors to plant recalcitrance. Lignins are composed primarily of syringyl (S), guaiacyl (G) and p-hydroxyphenyl (H) monolignol subunits, which are derived from sinapyl, coniferyl and p-coumaryl alcohols, respectively. The subunit ratio and resulting structure of plant lignins varies according to the genotype, environment, tissue type and maturity of the plant and as such, lignins are very heterogeneous and can vary significantly between different plants, within different tissues of a single plant and even within a single plant cell (Simmons B A et al., Curr Opin Plant Biol. 13:313-20 (2010)). This complexity and heterogeneity hinders the development of conversion technology able to process a range of sustainable feedstocks in a cost-effective manner. A lack of precise understanding of this structure has been an impediment in designing biomass improvement and biomass conversion strategies.

An increase in cellulose and a reduction of lignin content and cell wall recalcitrance, is desirable for biofuel, and pulp and paper industries. Conversely, increases in lignin content of cell walls can be desirable for production of lignin-based products such as carbon fibers. Thus, genetic manipulation of biomass feedstock to modulate cellulose and lignin biosynthesis, and sugar release efficiency hold promise both for production of improved, economically sustainable lignocellulosic biofuels (Vermerris W. et al., Crop Science 47(S3): S142-S153 (2007); Fu C. et al., PNAS 108:3803-3808 (2011)), and for creating improved cellulose- and lignin-based bioproducts.

The genus Populus represents an economically important tree crop that has been targeted for use in diverse applications from the pulp and paper industry, bioremediation, carbon sequestration and as a feedstock in the lignocellulosic biofuel industry (Dinus R J. et al., Crit. Rev. Plant Sci. 20:51-69 (2001)). Recent molecular profiling (using transcriptomics, proteomics and bioinformatics) and analysis of developmental (xylem development, [Kalluri et al., 2009]) and physiological (tension stress response) conditions under which, perennial plants such as Populus undergo enhanced cellulose biosynthesis, secondary cell wall development and biomass production has identified new genes that potentially impact biomass properties (Yang et al., 2011).

Tension wood is a special type of reaction wood formed in upper side of bending/leaning stems of woody angiosperms, and is characterized enhanced xylem (wood) cell proliferation, cellulose production in new cell wall layers [>90% cellulose], and reduced recalcitrance (Foston et al., 2001; Jung et al., 2013). Molecular profiling of tension stress response is an effective approach to understanding the biosynthetic, signaling and regulatory factors profiling underlying tension wood formation.

Recently, a study using wild Populus trichocarpa genotypes collected in the Pacific Northwest region demonstrated high phenotypic variation among the accessions in recalcitrance measured by lignin content and sugar release (Studer M H. et al., PNAS 108:6300-6305 (2011)). This study suggested that sufficient variation occurs in wild germplasm to identify specific genetic determinants of the recalcitrance trait by analysis of naturally-occurring allelic variability.

Quantitative trait loci (QTL) studies have been conducted using interspecific mapping of populations to identify genomic regions associated with cell wall phenotypes linked to recalcitrance (Novaes E. et al., *New Phytologist* 182:878-890 (2009); Yin T. et al., *PLoS one* 5:e14021 (2010)). Wegrzyn J L. et al., *New Phytologist* 188:515-532 (2010) demonstrated the feasibility of using linkage disequilibrium (LD)-based association mapping to validate candidate genes with putative functions in cell wall biosynthesis. The extent of LD decay in *P. trichocarpa* has been described by Slavov G T. et al., *New Phytologist* 196(3):713-25 (2012), who reported LD decay to below $r^2=0.2$ within 2 kb in more than half of the genes, within a genomewide average 6-7 kb. Given that the average gene size for *P. trichocarpa* is 5 kb, these results suggest that QTL fine-mapping and association mapping to within single-gene resolution is possible in *P. trichocarpa*.

Identification and manipulation of genes regulating cell wall biosynthesis and recalcitrance is critical both for efficient production of cellulosic sugars and ethanol from plant biomass, and for production of improved cellulose-based products, such as paper and pulp and nanocellulose composites.

SUMMARY OF THE INVENTION

This disclosure provides plants having improved biomass properties of increased biomass quantity and density, increased cellulose content and deceased lignin content and improved sugar release efficiency, methods of generating (genetically modifying) and/or selecting (natural variant collections) plants with such preferred attributes of cellulose, lignin and sugar release, and uses of such plants. The inventors have determined that the expression of the gene, Potri.001G375700 (SEQ. ID. NO: 1) (belonging to IQD signaling protein family containing a canonical calmodulin-binding domain) and/or activity of Potri.001G375700, modulates cellulose, lignin synthesis, sugar release and growth in plants. Plants with improved biomass properties (increased cellulose or decreased lignin) and increased sugar release efficiency, based on the expression or activity of the Potri.001G375700 gene, have divergent uses including pulp and paper production, lignin-based carbon fibers and ethanol/biofuel production.

In one embodiment, methods of generating and/or selecting a plant for improved biomass characteristics are provided. The methods include the steps of (a) obtaining nucleic acids from a candidate plant; (b) DNA construct development or regulating expression of target gene; (c) selecting a plant based on the presence of an allelic variant of the IQD gene in the nucleic acids obtained from the plant; (d) clarifying phenotypes associated with altered sequence or expression of gene.

Disclosed herein are nucleic acid inhibitors of expression of Potri.001G375700 gene, or inhibitors of expression of allelic variants of Potri.001G375700 gene, which can be used to reduce expression of the Potri.001G375700 gene and allelic variants thereof, to increase cellulose and reduce lignin biosynthesis, and increase sugar release. Specific nucleic acid inhibitors include antisense RNA, small interfering RNA, RNAi, microRNA, artificial microRNA, and ribozymes. Inhibitors of Potri.001G375700 gene activity include vectors or plasmids expressing nucleic acids specific to the target, SEQ ID NO: 1, (for example, an RNAi hairpin loop structure consisting of sense and antisense sequences representative of a gene-specific region in target), operably linked to a regulatory region that is functional in a plant.

Also disclosed herein are plants and plant cells genetically modified by introduction of the disclosed inhibitors and expression vectors. Expression of such inhibitors and expression vectors in a plant or plant cell can be used in methods to increase glucose and/or xylose release in a plant or plant cell, to increase cellulose content, to increase growth, or to decrease lignin synthesis, in such genetically modified plants and plant cells. Further disclosed herein are improved methods of producing biofuel from cellulosic biomass, by using plants with reduced or inhibited expression or activity of the Potri.001G375700 gene in biofuel production processes.

Further disclosed herein is an allelic variant of Potri.001G375700 can encode a protein having the amino acid sequence that is shorter (truncated), longer (frameshift or indel) or identical (amino acid replacement) relative to the reference gene Potri.001G375700 gene (SEQ. ID NO: 1). In one example, the allelic variant carries an indel or frameshift mutation ["CA to CA/CAA" nucleotide variation at position 39065790 and/or "AA to AA/AACA" nucleotide position at position 39065847 of chromosome number one]. Methods to determine nucleic acid sequences are known in the art and include, for example, polymerase chain reaction and sequencing.

This disclosure further provides expression vectors with a nucleotide sequence encoding the polypeptide encoded by SEQ ID NO: 1, or another allelic variant of Potri.001G375700 gene, operably linked to a regulatory region that is functional in a plant. The regulatory region can be a promoter with ubiquitous expression, an inducible promoter or a tissue-specific promoter, for example, a xylem-specific promoter. Further provided herein are plants and plant cells genetically modified by introduction of such expression vectors, and methods for improving desirable biomass properties in a plant or plant cell by expressing such expression vectors in a plant or plant cell of interest.

Additionally disclosed are methods of producing paper and pulp, by using plants with increased expression of the Potri.001G375700 gene in paper or pulp production processes. Further disclosed are pulp and paper products produced by this method, using plants with increased expression of the Potri.001G375700 gene.

DETAILED DESCRIPTION OF THE INVENTION

Figure 1:
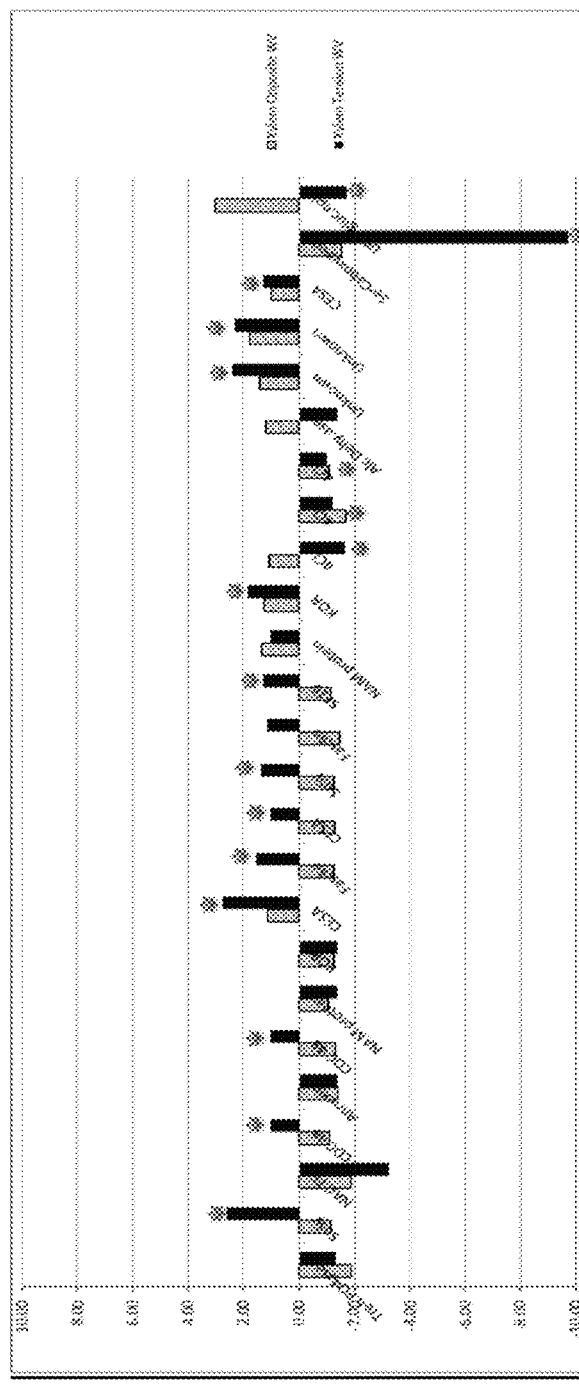
FIG. 1. qRTPCR expression profile of candidate cellulose and lignin pathway genes in xylem libraries obtained from a tension stress response study. Black colored bars represent tension-side response and grey dotted bars represent opposite-side response. Significant differential expression between tension and opposite sides are identified with asterisks. Genes are plotted on x-axis and identified with their gene descriptions. "SF16" represents the gene PoptrIQD/PdIQD, which is shown here are upregulated on tension-side (black bar). Data represents means±SE (n=3).

Disclosed herein are plants having improved biomass properties of increased biomass quantity and density, increased cellulose content and decreased lignin content and improved sugar release efficiency, methods of generating genetically modifying plants and/or selecting plants with improved biomass properties, and uses of such plants. The inventors have identified a gene, denoted Potri.001G375700 (SEQ. ID. NO: 1), that modulates plant biomass quantity and quality (i.e., cellulose content and crystallinity, lignin content and S/G ratio, and sugar release and bioethanol production. Potri.001G375700 gene encodes a putative calmodulin-binding signaling protein belonging to the IQD gene family. Plants with modulated (increased or decreased) cellulose and lignin synthesis and sugar release characteristics, based on modulation of the expression or activity of Potri.001G375700 gene, have divergent uses including pulp and paper, and nanocellulose production, ethanol/biofuel production, and in belowground carbon cycling and sequestration via altered belowground biomass and recalcitrance to soil microbes.

The inventors have discovered new naturally occurring alleles in *Populus trichocarpa* associated with cell wall phenotypes. The inventors have determined that an alternate route to decrease the levels of the functional protein product, more specifically single nucleotide polymorphism in specific sites within the gene Potri.001G375700, which result in missense mutation and predicted truncated protein product, also leads to a plant with desirable biomass properties (of increased biomass quantity and density, increased cellulose content and deceased lignin content and improved sugar release efficiency) suitable for uses including biofuel production and pulp production.

Disclosed also herein are nucleic acid inhibitors of expression of Potri.001G375700, or inhibitors of expression of allelic variants of Potri.001G375700, which can be used to reduce expression of the Potri.001G375700 gene and allelic variants thereof, to provide high cellulose, low lignin biosynthesis and high sugar release.

Potri.001G375700 Alleles and Sequences

The inventors have studied the effects of Potri.001G375700 gene. Analysis of genome resequencing and biomass phenotyping data for Potri.001G375700 gene over 500 different genotypes in the *Populus trichocarpa* natural variation and association study population revealed a frameshift mutation, ["CA to CA/CAA" nucleotide variation at position 39065790 and/or "AA to AA/AACA" nucleotide position at position 39065847 of chromosome number one], predicted to result in coding of missense proteins corresponding to locus Potri.001G375700 gene associated with traits of desirable biomass properties.

Allelic Variants of Potri.001G375700

As used herein, "allelic variants" are alternative forms (sequence variants of similar lengths of truncated versions with significant portions of "reference/*P. trichocarpa* nisquallyl genotype" allele missing) of the same gene or genetic locus. Each allelic variant has a distinct nucleic acid sequence at the locus of interest. Allelic variants can encode functionally different proteins when the difference in nucleic acid sequence result in even one alteration or deletion in the amino acid sequence between the variants or can encode a frameshift or truncated polypeptide relative to the sequence of the protein encoded by SEQ ID NO: 1 (*P. trichocarpa* nisquallyl reference sequence). Where one allelic variant encodes a truncated protein relative to the protein encoded by another allelic variant, percent identity can be determined by comparing the amino acid sequences of the variants along the length of the shorter protein. Allelic variation caused by an indel (s) in the Potri.001G375700 gene is associated with improved biomass properties of increased biomass quantity, increased cell wall sugar content and deceased lignin content and improved sugar release efficiency.

"Sugar release characteristics" include high or low release of sugars, also referred to as low or high recalcitrance. "High" sugar release (i.e., low recalcitrance) means that sugar can be extracted more easily, or more sugar can be extracted, from a plant, under conditions that would result in less sugar release in a plant without the particular allelic variant. "Low" sugar release (i.e., high recalcitrance) means that sugar can be extracted less easily, or less sugar can be extracted, from a plant, under conditions that would result in more sugar release in a plant without the particular allelic variant. In one example, sugar release refers to the amount of 5- and 6-carbon sugars that can be recovered from a plant using standard techniques to extract these sugars from plant materials. Sugars that can be released include, but are not limited to, glucose, xylose, fructose, arabinose, lactose, ribose, mannose, galactose, and sucrose. Examples of 5-carbon sugars (pentoses) include xylose, ribose, and arabinose; examples of 6-carbon sugars include glucose, fructose, mannose, and galactose.

Sugar release can be measured, for example, by saccharification analysis. In one example of saccharification analysis, sugars are extracted with alpha-amylase and (3-glucosidase in sodium acetate, followed by an ethanol soxhlet extraction. After drying overnight, water is added, and samples are sealed and reacted. Once cooled, a buffer-enzyme mix with cellulose oxidative enzymes is added and incubated with the sample. After incubation, an aliquot of the saccharified hydrolysate is tested for sugar content/release, such as by addition of glucose oxidase/peroxidase for measuring glucose content, and/or xylose dehydrogenase to measure xylose content.

Cellulose, a homopolymer of beta 1-4-linked D-glucose units and the most abundant component of secondary cell walls, is synthesized by integral membrane protein complex (CSC) composed on CesA or cellulose synthase proteins. The cellulose properties of quantity, degree of polymerization and crystallinity vary across species, across genotypes of a species and within cell types of an individual plant. Cellulose quantity and quality are significant considerations in selection of feedstocks for cellulosic biofuel or bioproduct production. Cellulose content, crystallinity and degree of polymerization can be affected by modifying the expression of Potri.001G375700 gene in plant.

Measuring Cellulose in Plants

Cellulose was estimated from air-dried stem (wood) sample using anthrone method (Updegraff, 1969). Stem sample (25 mg) was first digested with 500 µl of acetic-nitric acid reagent (100 ml of 80% acetic acid mixed with 10 ml of nitric acid) at 98° C. for 30 min. After cooling, the sample was centrifuged, discarded the supernatant, and washed with water. After brief centrifugation, water was discarded and the pellet was digested with 67% (v/v) sulfuric acid for 1 hr at room temperature. An aliquot of the mix was diluted (1:10) with water. In a PCR tube, 10 μl of diluted reaction mix, 40 μl of water and 100 μl of freshly prepared anthrone reagent (0.5 mg anthrone ml-1 of cold concentrated sulfuric acid) were added and heated for 10 min at 96° C. Samples were cooled and absorbance (A630) was measured. Cellulose was then estimated based on the absorbance of glucose standards. C6 sugar levels were also estimated by MBMS profiling and wet chemistry methods. Cellulose crystallinity was determined by NMR. Methods of measuring these cellulose properties in biomass are known in the art; see, for example, Foston et al. 2009 and Sluiter A. et al., Determination of structural carbohydrates and lignin in biomass—laboratory analytical procedure. Technical Report NREL/P-510-42618:1-17 (2008), available from the National Renewable Energy Laboratory.

Lignin" is a complex polymer composed of monolignol subunits, primarily syringyl (S), guaiacyl (G) and p-hydroxyphenyl (H) monolignols, derived from sinapyl, coniferyl and p-coumaryl alcohols, respectively. Lignin forms strong bonds with sugars and interferes with access to these carbohydrates, making it difficult to extract the plant's sugars contained in cellulose and hemicellulose. Differences in lignin content alters the sugar release properties of a plant in the extraction process. Lower lignin levels in a plant are associated with higher levels of sugar release, while higher lignin levels are associated with lower levels of sugar release. Thus, sugar release and lignin content can show an inverse correlation. Lignin content, ratio or amount of monolignols, and expression and/or activity of lignin biosynthetic enzymes, can be affected by modifying the expression of Potri.001G375700 gene in plant.

Measuring Lignin Synthesis

Methods to determine if a plant has altered lignin synthesis include, for example, directly measuring lignin content, or by determining the expression or activity of genes in the lignin biosynthetic pathway. Lignin content can be measured directly, for example, by thioglycolysis, or by histochemical analysis of tissue sections stained with toluidine blue O (TBO), Wiesner reagent, or Maule reagent to identify lignified or non-lignified cell walls. Liginin may also be measured by pyrolysis vapor analysis using pyrolysis Molecular Beam Mass Spectrometry (py-MBMS) (Evans R J. et al., *Energy and Fuels* 1:123-137 (1987); Sykes R. et al., *Biofuels: Methods and Protocols* 169-183 (2009); Tuskan G. et al., *Appl. Biochem. Biotechnol.* 77:55-65 (1999)). Additional methods of measuring carbohydrate and lignin content in biomass are known in the art; see, for example, Sluiter A. et al., Determination of structural carbohydrates and lignin in biomass—laboratory analytical procedure. Technical Report NREL/TP-510-42618:1-17 (2008), available from the National Renewable Energy Laboratory.

Methods to Generate and Select Plants with Improved Biomass Properties.

In one embodiment, methods of generating and selecting a plant for improved biomass properties of increased biomass quantity, increased cell wall sugar content and deceased lignin content and improved sugar release efficiency are provided. The methods include the steps of (a) obtaining nucleic acids from a candidate plant; (b) design, construction, delivery and verification of integration in host plant (*Populus deltoides*) genome of a RNAi gene down-regulation construct for Potri.001G375700 target gene; and (c) selection of plants (carrying RNAi construct of Potri.001G375700 with improved biomass properties based as determined by quantitative analysis of stem biomass, cellulose and lignin content, and sugar release and/or ethanol production using existing art.

The first step in generating and selecting a plant with modified expression of target gene Potri.001G375700 is to obtain (a) experimental evidence (gene expression context) in support of potential molecular role and secondly, (b) validating the functional role (via RNAi transgene technology and SNP association analysis) in impacting biomass properties nucleic acids from a candidate plant. Experimental evidence in support of a potential molecular role for the target gene Potri.001G375700, belonging to the IQD gene family, described here was originally identified by the inventors as highly expressed in developing xylem tissue, especially under tension stress. Co-expression analyses of in-house and publicly available datasets confirmed the expression context during biomass formation and suggesting a potential role. Validation of the functional role was undertaken by generating RNAi plants with down regulated levels of target gene expression Potri.001G375700 and detailed characterization of such plants for changes in biomass properties.

Methods of obtaining nucleic acids from a candidate plant, detecting the presence of a nucleotide sequence and constructing DNA clones (enzyme based amplification, sequencing, digestion, ligation and recombination) are known in the art. Nucleic acid can be isolated from a plant tissue sample, according to standard methodologies (Sambrook et al., Molecular Cloning, 2nd ed., Cold Spring Harbor Laboratory Press, CSH, 1.38-1.39, 1989).

A number of template dependent processes are available to amplify the marker sequences present in a given nucleic acid sample. One of the best known amplification methods is the polymerase chain reaction (referred to as PCR). Other methods of amplification are ligase chain reaction (LCR), Qbeta Replicase, isothermal amplification, strand displacement amplification (SDA), PCR-like template- and enzyme-dependent synthesis using primers with a capture or detector moiety, transcription-based amplification systems (TAS), cyclical synthesis of single-stranded and double-stranded DNA, "RACE", one-sided PCR, and di-oligonucleotide amplification.

The PCR method is well known in the art and disclosed, for example, in WO 99/28500; Sambrook et al. (Molecular Cloning—A Laboratory Manual, Cold Spring Harbor Laboratory, Cold Spring Harbor, N.Y. 1989); Nucleic Acid Hybridization (Hames and Higgins eds., 1984); and Current Protocols in Human Genetics (Dracopoli et al., eds, 1984 with quarterly updates, John Wiley & Sons, Inc.), all of which are incorporated herein by reference. The PCR method utilizes a pair of oligonucleotide primers, each hybridizing to one strand of a double-stranded DNA/RNA target. The primers flank the region that will be amplified. The PCR method comprises contacting the primers and target sequence, or mixture of target sequences and optional polynucleotide probes, and performing the amplification steps.

Primers for nucleic acid amplification of the Potri.001G375700 gene should contain a hybridizing region exactly or substantially complementary or corresponding to a target nucleotide sequence. Primer extension is performed under hybridization conditions of sufficient stringency to allow the selective amplification of the target sequence. A primer can either consist entirely of the hybridizing region or can contain additional features which allow for detection, immobilization, or manipulation of the amplified product, but which do not alter the basic property of the primer (that is, acting as a point of initiation of DNA synthesis).

The generation of plants with altered activity of the gene (s) orthologous to the gene Potri.001G375700 in other crops species and/or selection of nonsynonymous or missense allelic variants of the gene(s) orthologous to the Potri.001G375700 gene in other crop species allows for generation, selection and/or screening of candidate plants for having improved sugar release or biomass formation characteristics. These biomass characteristics include a combination of high or low sugar release, such as high or low release of glucose and/or xylose, high or low biomass quantity or density and high or low cellulose or lignin levels. Preferred characteristics include, high biomass, high cellulose and high release of glucose and/or xylose.

Selection and Screening Using the Potri.001G375700 Gene

The gene Potri.001G375700 expression can be modified using transgenic technology or sequence of an allelic variant of the Potri.001G375700 gene resulting in decreased gene activity, can be used as a molecular marker for use in screening germplasm in plant breeding and genetic improvement efforts.

Inhibitors and Expression Vectors for Modulating the Activity of Potri.001G375700

Disclosed herein are nucleic acid inhibitors of expression of Potri.001G375700, or inhibitors of expression of allelic variants of Potri.001G375700, which can be used to reduce expression of the Potri.001G375700 gene and allelic variants thereof, to provide high cellulose and low lignin biosynthesis, and high sugar release and ethanol production. Specific nucleic acid inhibitors include antisense RNA, small interfering RNA, RNAi, microRNA, artificial microRNA, site-specific recombination gene cassettes and ribozymes. Inhibitors of Potri.001G375700 activity include expression vectors encoding the polynucleotide of SEQ ID NO: 1, operably linked to a regulatory region that is functional in a plant.

The polynucleotides and expression vectors described herein can be used to increase or inhibit expression of Potri.001G375700 or a Potri.001G375700 allelic variant. The term "expression" refers to the process of converting genetic information of a polynucleotide into RNA through transcription, which is catalyzed by an enzyme, RNA polymerase and into protein, through translation of mRNA on ribosomes. Up-regulation or overexpression refers to regulation that increases the production of expression products (mRNA, polypeptide or both) relative to basal or native states, while inhibition or down-regulation refers to regulation that decreases production of expression products (mRNA, polypeptide or both) relative to basal or native states.

A "nucleic acid inhibitor" is a nucleic acid that can reduce or prevent expression or activity of a target gene. For example, a nucleotide structure designed to recognize and reduce or eliminate the native Potri.001G375700 nucleotide messages or inhibit expression of Potri.001G375700 can reduce or eliminate transcription and/or translation of the Potri.001G375700 gene product, thus reducing Potri.001G375700 protein expression and activity.

An altered level of gene expression refers to a measurable or observable change in the level of expression of a transcript of a gene, or the amount of its corresponding polypeptide, relative to a control plant or plant cell under the same conditions (e.g., as measured through a suitable assay such as quantitative RT-PCR, a Northern blot, a Western blot or through an observable change in phenotype, chemical profile or metabolic profile). An altered level of gene expression can include up-regulated or down-regulated expression of a transcript of a gene or polypeptide relative to a control plant or plant cell under the same conditions. Altered expression levels can occur under different environmental or developmental conditions or in different locations than those exhibited by a plant or plant cell in its native state.

Techniques for introducing nucleic acids (inhibitors and expression vectors) into monocotyledonous and dicotyledonous plants are known in the art and include, without limitation, *Agrobacterium*-mediated transformation, viral vector-mediated transformation, electroporation and particle gun transformation, e.g., U.S. Pat. Nos. 5,538,880, 5,204, 253, 6,329,571 and 6,013,863. If a cell or tissue culture is used as the recipient tissue for transformation, plants can be regenerated from transformed cultures if desired, by techniques known to those skilled in the art. See, e.g., Niu et al., *Plant Cell Rep*. V19:304-310 (2000); Chang and Yang, *Bot. Buff Acad. Sin.*, V37:35-40 (1996) and Han et al., *Biotechnology in Agriculture and Forestry*, V44:291 (ed. by Y. P. S. Bajaj), Springer-Vernag, (1999).

Nucleic Acid Inhibitors

A number of nucleic acid based methods, including antisense RNA, ribozyme directed RNA cleavage, post-transcriptional gene silencing (PTGS), e.g., RNA interference (RNAi), microRNA and artificial microRNA and transcriptional gene silencing (TGS) can be used to inhibit Potri.001G375700 expression in plants. Suitable inhibitors include full-length nucleic acids of allelic variants of Potri.001G375700, or fragments of such full-length nucleic acids. In some embodiments, a complement of the full-length nucleic acid or a fragment thereof can be used. Typically, a fragment is at least 10 nucleotides, e.g., at least 12, 13, 14, 15, 16, 17, 18, 19, 20, 21, 22, 23, 24, 25, 26, 27, 30, 35, 40, 50, 80, 100, 200, 500 nucleotides or more. Generally, higher homology can be used to compensate for the use of a shorter sequence.

Antisense technology is one well-known method. In this method, a nucleic acid segment from a gene to be repressed is cloned and operably linked to a regulatory region and a transcription termination sequence so that the antisense strand of RNA is transcribed. The recombinant vector is then transformed into plants, as described below and the antisense strand of RNA is produced. The nucleic acid segment need not be the entire sequence of the gene to be repressed, but typically will be substantially complementary to at least a portion of the sense strand of the gene to be repressed.

In another method, a nucleic acid can be transcribed into a ribozyme or catalytic RNA, which affects expression of an mRNA. See, U.S. Pat. No. 6,423,885. Ribozymes can be designed to specifically pair with a target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes cleave mRNAs at locations dictated by flanking regions that form complementary base pairs with the target mRNA. See, for example, U.S. Pat. No. 5,254,678; Perriman et al., *PNAS* 92(13):6175-6179 (1995); de Feyter and Gaudron, Methods in Molecular Biology, Vol. 74, Chapter 43, Edited by Turner, P. C., Humana Press Inc., Totowa, N.J. RNA endoribonucleases which have been described, such as the one that occurs naturally in *Tetrahymena thermophila*, can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence or a fragment thereof, of the polypeptide of interest. The length of the sequence that is similar or identical to the sense coding sequence can be from 10 nucleotides to 500 nucleotides, from 15 nucleotides to 300 nucleotides, from 20 nucleotides to 100 nucleotides or from 25 nucleotides to 100 nucleotides. The other strand of the stem portion of a double stranded RNA comprises a sequence that is similar or identical to the antisense strand or a fragment thereof, of the coding sequence of the polypeptide of interest and can have a length that is shorter, the same as or longer than the corresponding length of the sense sequence. In some cases, one strand of the stem portion of a double stranded RNA comprises a sequence that is similar or identical to the 3' or 5' untranslated region or a fragment thereof, of the mRNA encoding the polypeptide of interest and the other strand of the stem portion of the double stranded RNA comprises a sequence that is similar or identical to the sequence that is complementary to the 3' or 5' untranslated region, respectively or a fragment thereof, of the mRNA encoding the polypeptide of interest. In other embodiments, one strand of the stem portion of a double stranded RNA comprises a sequence that is similar or identical to the sequence of an intron or a fragment thereof in the pre-mRNA encoding the polypeptide of interest and the other strand of the stem portion comprises a sequence that is similar or identical to the sequence that is complementary to the sequence of the intron or fragment thereof in the pre-mRNA.

A construct including a sequence that is operably linked to a regulatory region and a transcription termination sequence and that is transcribed into an RNA that can form a double stranded RNA, can be transformed into plants as described below. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330 and 20030180945.

In some embodiments, a construct containing a nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary. The sense or antisense sequence can be a sequence that is identical or complementary to the sequence of an mRNA, the 3' or 5' untranslated region of an mRNA or an intron in a pre-mRNA encoding a polypeptide of interest or a fragment of such sequences. In some embodiments, the sense or antisense sequence is identical or complementary to a sequence of the regulatory region that drives transcription of the gene encoding a polypeptide of interest. In each case, the sense sequence is the sequence that is complementary to the antisense sequence.

A nucleic acid having at least one strand that is a template for one or more sense and/or antisense sequences can be operably linked to a regulatory region to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand and one from the bottom strand. See, for example, Yan et al., *Plant Physiol.*, 141: 1508-1518 (2006). The two regulatory regions can be the same or different. The two transcripts can form double-stranded RNA molecules that induce degradation of the target RNA. In some cases, a nucleic acid can be positioned within a P-DNA such that the left and right border-like sequences of the P-DNA are on either side of the nucleic acid.

In some embodiments, a suitable nucleic acid inhibitor can be a nucleic acid analog. Nucleic acid analogs can be modified at the base moiety, sugar moiety or phosphate backbone to improve, for example, stability, hybridization or solubility of the nucleic acid. Modifications at the base moiety include deoxyuridine for deoxythymidine and 5-methyl-2'-deoxycytidine and 5-bromo-2'-deoxycytidine for deoxycytidine. Modifications of the sugar moiety include modification of the T hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring or peptide nucleic acids, in which the deoxyphosphate backbone is replaced by a pseudopeptide backbone and the four bases are retained. See, for example, Summerton and Weller, 1997, *Antisense Nucleic Acid Drug Dev.*, 7:187-195; Hyrup et al., *Bioorgan. Med. Chem.*, 4:5-23 (1996). In addition, the deoxyphosphate backbone can be replaced with, for example, a phosphorothioate or phosphorodithioate backbone, a phosphoroamidite or an alkyl phosphotriester backbone.

Expression Vector Modulators of Potri.001G375700 and Uses Thereof.

This disclosure provides methods of altering biomass properties, specifically, increasing biomass quantity and density, increasing cellulose content and decreasing lignin content and recalcitrance, in a plant, comprising introducing into a plant cell an exogenous nucleic acid with a regulatory region operably linked to a nucleic acid encoding a Potri.001G375700 allelic variant, where a tissue of a plant produced from the plant cell has an altered cell wall compared to the cell wall in tissue of a control plant that does not comprise the nucleic acid. Alternate approaches include replacement and/or site-specific integration of Potri.001G375700 nucleotide sequence cassette or a multi-gene cassette including Potri.001G375700 nucleotide sequence using targeted genome editing technologies such as CRISPR/Cas9.

Vectors containing nucleic acids such as those described herein are provided. A "vector" is a replicon, such as a plasmid, phage or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs or PACs. The term "vector" includes cloning and expression vectors, as well as viral vectors and integrating vectors. An "expression vector" is a vector that includes a regulatory region. Suitable expression vectors include, without limitation, plasmids and viral vectors derived from, for example, bacteriophage, baculoviruses and retroviruses. Numerous vectors and expression systems are commercially available from such corporations as Novagen (Madison, Wis.), Clontech (Mountain View, Calif.), Stratagene (La Jolla, Calif.) and Invitrogen/Life Technologies (Carlsbad, Calif.).

The vectors provided herein also can include, for example origins of replication, scaffold attachment regions (SARs) and/or markers. A marker gene can confer a selectable phenotype on a plant cell. For example, a marker can confer biocide resistance, such as resistance to an antibiotic (e.g., kanamycin, G418, bleomycin or hygromycin) or an herbicide (e.g., chlorosulfuron or phosphinothricin). In addition, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin or Flag-tag (Kodak, New Haven, Conn.) sequences typically are expressed as a fusion with the encoded polypeptide. Such tags can be inserted anywhere within the polypeptide, including at either the carboxyl or amino terminus. As described herein, plant cells can be transformed with a recombinant nucleic acid construct to express a polypeptide of interest.

The term "regulatory region" refers to a nucleic acid having nucleotide sequences that influence transcription or translation initiation and rate and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns and combinations thereof.

The term "operably linked" refers to positioning of a regulatory region and a sequence to be transcribed in a nucleic acid so as to influence transcription or translation of such a sequence. For example, to bring a coding sequence under the control of a regulatory region, the translation initiation site of the translational reading frame of the polypeptide is typically positioned between one and about fifty nucleotides downstream of the promoter. A regulatory region can, however, be positioned as much as about 5,000 nucleotides upstream of the translation initiation site or about 2,000 nucleotides upstream of the transcription start site. A regulatory region typically comprises at least a core (basal) promoter.

A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene (Fromm et al., *The Plant Cell* 1:977-984 (1989)). The choice of regulatory regions to be included depends upon several factors, including, but not limited to, efficiency, selectability, inducibility, desired expression level and cell- or tissue-preferential expression. It is a routine matter for one of skill in the art to modulate the expression of a coding sequence by appropriately selecting and positioning regulatory regions relative to the coding sequence.

A variety of promoters are available for use, depending on the degree of expression desired. For example, a broadly expressing promoter promotes transcription in many, but not necessarily all, plant tissues. Non-limiting examples of broadly expressing promoters that can be included in the nucleic acid constructs provided herein include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter and ubiquitin promoters such as the maize ubiquitin-1 promoter.

Some suitable regulatory regions initiate transcription, only or predominantly, in certain cell types. For example, a promoter that is active predominantly in a reproductive tissue (e.g., fruit, ovule or inflorescence) can be used. Thus, as used herein a cell type- or tissue-preferential promoter is one that drives expression preferentially in the target tissue, but may also lead to some expression in other cell types or tissues as well.

Root-active and root-preferential promoters confer transcription in root tissue, e.g., root endodermis, root epidermis or root vascular tissues. Root-preferential promoters include the root-specific subdomains of the CaMV 35S promoter (Lam et al., *Proc. Natl. Acad. Sci. USA*, 86:7890-7894 (1989)), root cell specific promoters reported by Conkling et al., *Plant Physiol.*, 93:1203-1211 (1990) and the tobacco RD2 promoter. Potential uses of modified activity of Potri.001G375700 in roots include to impact belowground biomass quality and decomposition rate, two critical contributions of plant to belowground carbon cycling and sequestration processes and plant microbe interactions.

Promoters active in photosynthetic tissue confer transcription in green tissues such as leaves and stems. Examples of such promoters include the ribulose-1,5-bisphosphate carboxylase (RbcS) promoters such as the RbcS promoter from eastern larch (*Larix laricina*), the pine cab6 promoter (Yamamoto et al., *Plant Cell Physiol.*, 35:773-778 (1994)), the Cab-1 promoter from wheat (Fejes et al., *Plant Mol. Biol.*, 15:921-932 (1990)), the CAB-1 promoter from spinach (Lubberstedt et al., *Plant Physiol.*, 104:997-1006 (1994)), the cab IR promoter from rice (Luan et al., *Plant Cell*, 4:971-981 (1992)), the pyruvate orthophosphate dikinase (PPDK) promoter from corn (Matsuoka et al., *Proc. Natl. Acad. Sci. USA*, 90:9586-9590 (1993)), the tobacco Lhcb1*2 promoter (Cerdan et al., *Plant Mol. Biol.*, 33:245-255 (1997)), the *Arabidopsis* SUC2 sucrose-H+ symporter promoter (Truernit et al., *Planta*, 196:564-570 (1995)) and thylakoid membrane protein promoters from spinach (psaD, psaF, psaE, PC, FNR, atpC, atpD, cab, rbcS).

Lignin biosynthesis promoters are promoters that drive transcription of nucleic acids encoding enzymes involved in lignin biosynthesis. Examples of lignin biosynthesis promoters include promoters of the switchgrass (*Panicum virgatum*), rice (*Oryza sativa*), corn (*Zea mays*) and wheat (*Triticum aestivum*) homologs of the *Populus* cinnamate 4-hydroxylase, caffeoyl-CoA O-methyltransferase and caffeic acid O-methyltransferase genes. Also suitable are promoters of *Arabidopsis* genes encoding phenylalanin ammonia lyase (genomic locus At3g10340), trans-cinnamate 4-hydroxylase (genomic locus At2g30490), 4-coumarate:CoA ligase (genomic locus At1g51680), hydroxycinnamoyl-CoA:shikimate/quinate hydroxycinnamoyltransferase (genomic locus At5g48930), p-coumarate 3-hydroxylase (genomic locus At2g40890), caffeoyl-CoA 3-O-methyltransferase (genomic locus At4g34050), cinnamoyl CoA reductase (genomic locus At1g15950), ferulate 5-hydroxylase (genomic locus At4g36220), caffeic acid O-methyltransferase (genomic locus At5g54160) and cinnamyl alcohol dehydrogenase (genomic locus At4g34230).

Useful promoters also include cell wall related promoters, such as cellulose biosynthesis promoters. Cellulose biosynthesis promoters are promoters that drive transcription of nucleic acids encoding enzymes involved in cellulose biosynthesis. Examples of cellulose biosynthesis promoters include the promoter of the rice cellulose synthase gene (genomic locus Os08g25710), the promoter of the rice cellulose synthase gene (genomic locus Os08g06380) and the promoter of the rice cellulose synthase-like A2 gene (genomic locus Os10g26630).

Examples of promoters that have high or preferential activity in vascular bundles include the glycine-rich cell wall protein GRP 1.8 promoter (Keller and Baumgartner, *Plant Cell*, 3(10):1051-1061 (1991)), the *Commelina* yellow mottle virus (CoYMV) promoter (Medberry et al., *Plant Cell*, 4(2):185-192 (1992)) and the rice tungro bacilliform virus (RTBV) promoter (Dai et al., *Proc. Natl. Acad. Sci. USA*, 101(2):687-692 (2004)). Promoters having preferential activity in the phloem region (e.g., primary phloem cells, companion cells and sieve cells), the xylem region (e.g., tracheids and vessels), the bundle sheath layer and/or the endodermis are also considered vascular tissue promoters. Promoters that have preferential activity in the pith, cortex, epidermis and/or in the vascular bundles or vascular layers of the stem are considered stem promoters. In some cases, the activity of stein promoters can also be induced by stress like drought.

Inducible promoters confer transcription in response to external stimuli such as chemical agents or environmental stimuli. For example, inducible promoters can confer transcription in response to hormones such as gibberellic acid or ethylene or in response to light, nitrogen, shade or drought.

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

A 5' untranslated region (UTR) can be included in nucleic acid constructs described herein. A 5' UTR is transcribed, but is not translated and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a recombinant polynucleotide, e.g., introns, enhancers, upstream activation regions, transcription terminators and inducible elements. Thus, for example, more than one regulatory region can be operably linked to the sequence of a polynucleotide encoding a Gene Y homolog or other lignin-modulating polypeptide. Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

In one example, the coding sequence of gene Potri.001G375700 is amplified from either genomic DNA or cDNA by PCR. The DNA fragments are then subcloned into an expression construct.

Transgenic Plants/Plant Species/Plant Cells

Also disclosed herein are plants and plant cells genetically modified by introduction of the disclosed inhibitors and expression vectors including nucleic acids encoding a specific hairpin-loop fragments of one gene Potri.001G375700.

A plant or plant cell used in methods of the invention contains a recombinant nucleic acid construct as described herein. A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

Typically, transgenic plant cells used in methods described herein constitute part or all of a whole plant. Such plants can be grown in a manner suitable for the species under consideration, via propagation of seeds or vegetative cuttings (as in case of *Populus*) in a growth chamber, a greenhouse or in a field. Transgenic plants can be bred as desired for a particular purpose, e.g., to introduce a recombinant nucleic acid into other lines, to transfer a recombinant nucleic acid to other species or for further selection of other desirable traits. Progeny includes descendants of a particular plant or plant line provided the progeny inherits the transgene. Progeny of a plant include seeds formed on F1, F2, F3, F4, F5, F6 and subsequent generation plants or seeds formed on BC1, BC2, BC3 and subsequent generation plants or seeds formed on F1BC1, F1BC2, F1BC3 and subsequent generation plants. Seeds produced by a transgenic plant can be grown and then selfed (or outcrossed and selfed) to obtain seeds homozygous for the nucleic acid construct. Alternatively, transgenic plants can be propagated vegetatively for those species amenable to such techniques.

Transgenic plant cells growing in suspension culture or tissue or organ culture can be useful for extraction of polypeptides or compounds of interest, e.g., lignin monomers or compounds in a lignin biosynthetic pathway. For the purposes of this invention, solid and/or liquid tissue culture techniques can be used. When using solid medium, transgenic plant cells can be placed directly onto the medium or can be placed onto a filter film that is then placed in contact with the medium. When using liquid medium, transgenic plant cells can be placed onto a floatation device, e.g., a porous membrane that contacts the liquid medium. Solid medium typically is made from liquid medium by adding agar. For example, a solid medium can be any of various mineral salt media, e.g., Murashige and Skoog (MS) medium containing agar and a suitable concentration of an auxin, e.g., 2,4-dichlorophenoxyacetic acid (2,4-D) and a suitable concentration of a cytokinin, e.g., kinetin.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days or about 1-3 days. The use of transient assays is particularly convenient for rapid analysis in different species or to confirm expression of a heterologous Potri.001G375700 whose expression, subcellular localization and protein interaction partner has not previously been confirmed in particular recipient cells.

Initial and immediate application of the expression of Potri.001G375700 allelic variants can be made in the bioenergy crops *Populus* and switchgrass, but the application can be extended to other bioenergy crops such as corn, other sources of lignocellulosic biomass and other model plants e.g., *Salix, Miscanthus*, rice and *Medicago*.

For example, the polynucleotides and vectors described herein can be used to transform a number of monocotyledonous and dicotyledonous plants and plant cell systems, including alfalfa, ash, beech, birch, canola, cherry, clover, cotton, cottonseed, *eucalyptus*, flax, *jatropha*, mahogany, maple, mustard, oak, poplar, oilseed rape, rapeseed (high erucic acid and canola), red clover, teak, tomato, walnut and willow, as well as monocots such as barley, bluegrass, canarygrass, corn, fescue, field corn, millet, *miscanthus*, oat, rice, rye, ryegrass, *sorghum*, sudangrass, sugarcane, sweet corn, switchgrass, turf grasses, timothy and wheat. Gymnosperms such as fir, pine and spruce can also be suitable.

The methods and compositions can be used over a broad range of plant species, including species from the dicot genera *Acer, Afzelia, Arabidopsis, Betula, Brassica, Eucalyptus, Fagus, Fraxinus, Glycine, Gossypium, Jatropha, Juglans, Linum, Lycopersicon, Medicago, Micropus, Populus, Prunus, Quercus, Salix, Solanum, Tectona* and *Trifolium*; and the monocot genera *Agrostis, Avena, Festuca, Hordeum, Lemna, Lolium, Milium, Miscanthus oryza, Panicum, Pennisetum, Phalaris, Phleum, Poa, Saccharum, Secale, Sorghum, Triticum, Zea* and *Zoysia*; and the gymnosperm genera *Abies, Picea* and *Pinus*. In some embodiments, a plant is a member of the species *Festuca arundinacea, Miscanthus* hybrid (*Miscanthus×giganteus*), *Miscanthus sinensis, Miscanthus sacchariflorus, Panicum virgatum, Pennisetum purpureum, Phalaris arundinacea, Populus* spp including but not limited to *balsamifera, deltoides, tremuloides, tremula, alba* and *maximowiczii, Saccharum* spp., *Secale cereale, Sorghum almum, Sorghum halcapense* or *Sorghum vulgare*. In certain embodiments, the polynucleotides and vectors described herein can be used to transform a number of monocotyledonous and dicotyledonous plants and plant cell systems, wherein such plants are hybrids of different species.

In another aspect, a plant cell comprising a Potri.001G375700 nucleic acid inhibitor is provided. The plant cell comprises an exogenous nucleic acid, the exogenous nucleic acid comprising a regulatory region operably linked to a polynucleotide that is transcribed into an interfering RNA effective for inhibiting expression of Potri.001G375700. The exogenous nucleic acid can further comprise a 3' UTR operably linked to the polynucleotide. The polynucleotide can be transcribed into an interfering RNA comprising a stem-loop structure. The stem-loop structure can comprise an inverted repeat of the 3' UTR.

In another aspect, a plant is provided. The plant comprises any of the plant cells described above. Progeny of the plant also are provided, where the progeny have altered (increased or decreased) cellulose and lignin content.

Methods of Use of Transgenic Plants

Disclosed herein are methods to increase glucose and/or xylose release in a plant or plant cell, increase biomass quantity or density (in stems and/or root), increase cellulose biosynthesis or to decrease lignin synthesis (in stems and/or root), by expressing the disclosed inhibitors in plants and plant cells.

Further disclosed herein are improved methods of producing biofuel from cellulosic biomass, by using plants with reduced or inhibited expression or activity of the Potri.001G375700 gene in biofuel production processes. Methods of pretreatment and saccharification of biomass to fermentable sugars, followed by fermentation of the sugars to ethanol, are known in the art.

Articles of Manufacture

The materials and methods described herein are useful for modifying biomass characteristics, such as characteristics of biomass renewable energy source plants. "Biomass" refers to any cellulosic or lignocellulosic material and includes materials containing cellulose, and optionally further containing hemicellulose, lignin, starch, oligosaccharides and/ or monosaccharides. The term "cellulosic" refers to a composition containing cellulose. The term "lignocellulosic" refers to a composition containing both lignin and cellulose. According to the invention, biomass may be derived from a single source, or biomass can contain a mixture derived from more than one source; for example, biomass can contain a mixture of corn cobs and corn stover, or a mixture of grass and leaves. Examples of biomass include, but are not limited to, tree crops such as *Populus*, corn grain, corn cobs, crop residues such as corn husks, corn stover, grasses, wheat, wheat straw, barley, barley straw, hay, rice straw, switchgrass, waste paper, sugar cane bagasse, *sorghum*, soy, components obtained from processing of grains, trees, branches, roots, leaves, wood chips, sawdust, shrubs and bushes, vegetables, and fruits.

Lignin itself, which can be gathered from transgenic plants provided herein, can be converted into valuable fuel additives. Lignin can be recovered from any bioethanol production process using agricultural materials such as straw, corn stalks and switchgrass engineered to have increased lignin content. Lignin can be combusted to provide heat and/or power for the ethanol process; however, increasing the value of the lignin by converting it to higher value fuel additives can significantly enhance the competitiveness of bioethanol technology. Lignins removed from wood pulp as sulphates can be used as dust suppression agents for roads, as dispersants in high performance cement applications, water treatment formulations and textile dyes or as raw materials for several chemicals, such as vanillin, DMSA, ethanol, torula yeast, xylitol sugar and humic acid.

The invention also relates to the use of the pulp obtained from the disclosed genetically modified plants in the production of cellulose-based products, for example, in the paper industry, for the production of cardboard or for nanocellulose production. Pulp, produced using plants which have been genetically modified to have increased expression of the Potri.001G375700 gene and therefore also have increased lignin synthesis, can be used as a building material and in particular as output material for pressed chipboard, fiberboard of medium density, or as filler material.

Seeds of transgenic plants described herein can be conditioned and bagged in packaging material by means known in the art to form an article of manufacture. Packaging material such as paper and cloth are well known in the art. A package of seed can have a label, e.g., a tag or label secured to the packaging material, a label printed on the packaging material or a label inserted within the package. The package label may indicate that the seed herein incorporates transgenes that provide increased amounts of lignin or altered SIG lignin ratio in one or more tissues of plants grown from such seeds.

The present disclosure is further illustrated by the following non-limiting examples.

Further disclosed herein are methods for identifying suitable allelic variants, primers targeting conserved regions of the gene can be used to identify genotypes carrying alterations that lead to amino acid substitutions which can affect gene function.

A population of plants can be screened or selected for those members of the population that have a desired trait or phenotype. Selection or screening can be carried out over one or more generations, which can be useful to identify those plants that have a desired characteristic, such as high biomass content with low recalcitrance, low lignin synthesis, and/or high sugar release. Selection or screening can be carried out in more than one geographic location. In some cases, transgenic plants can be grown and selected under conditions which induce a desired phenotype or are otherwise necessary to produce a desired phenotype in a transgenic plant. In addition, selection or screening can be carried out during a particular developmental stage in which the phenotype is exhibited by the plant.

EXAMPLES

Example 1: Material and Methods

Phylogenetic Analysis:

Protein sequences of *Populus* WND isoforms were retrieved from Phytozome v9.1: *Populus trichocarpa* v3.0 and the rest from NCBI database. Phylogenetic analysis was performed in MEGA (Molecular Evolutionary Genetics Analysis) program using the Neighbor-Joining method. Bootstrap values were calculated from 500 independent bootstrap runs. Protein sequence alignment was performed using clustal W and shading and percent similarity were predicted by GeneDoc program.

Construct Development

RNAi construct was developed by amplifying a 156 bp nucleotide sequence overlapping the 3' coding region and UTR regions and ligating in sense and antisense orientation across CHS intron in the vector 156 bp coding region fragment, and ligated in sense and antisense orientation to form hairpin with chalcone synthase intron. The binary constructs was transformed into wild-type *P. deltoides* 'WV94' using *Agrobacterium* method (Caiping et al., 2004). For subcellular localization, full length coding region of PdIQD1 (Potri.001G375700) was amplified from *P. deltoides* xylem cDNA library (primers were listed in Supplemental file 1) using Q5 High-Fidelity DNA polymerase (New England Biolabs, Ipswich, Mass.) and cloned in pENTR vector (Invitrogen, Carlsbad, Calif., USA). After sequence confirmation, coding region fragment was recombined into a Gateway binary vector pGWB405 (Tsuyoshi et al., 2009) using LR clonase (Invitrogen). Plasmid from a positive clone was transformed to *Agrobacterium tumefaciens* strain GV3101. Tobacco infiltration and protein localization was performed as described previously (DePaoli et al., 2011; Sparkes et at, 2006). *Agrobacterium* harboring binary construct PdIQD1 or PdKLCR-1 were cultured overnight in LB media. After brief centrifugation, supernatant was removed and pellet was dissolved in 10 mM $MgCl_2$ and OD at A600 was adjusted to 0.5. The culture was infiltrated into 4-week old tobacco leaves. After 48 h, roughly 4 $mm^2$ leaf sections were cut and fixed in 3.7% formaldehyde, 50 mM $NaH_2PO_4$ and 0.2% Triton X-100 for 30 min, rinsed with phosphate-buffered saline (PBS) and stained in DAPI (4,6'-diamidino-2-phenylindole, 1.5 µg $ml^{-1}$ in PBS) for 30 min. GFP visualization and imaging was performed on Zeiss LSM710 confocal laser scanning microscope (Carl Zeiss Microscopy, Thornwood, N.Y.) equipped with a Plan-Apochromat 63×/1.40 oil immersion objective.

Plant Materials

Transgenic plants and empty-vector transformed control plants that were roughly 15-cm were moved from tissue culture to small tubes with soil. After 2-months, plants were moved to bigger pots (6 liter) and were propagated in a greenhouse maintained at 25° C. at 16 h day length. At the time of harvest (7-month old plants), plant height was measured from shoot tip to stem base, and diameter was measured at base of the stem. In our preliminary study, the bottom 10 cm stem portion was harvested, air-dried and used for carbohydrate composition, cellulose, lignin, S:G ratio, and sugar and ethanol release analysis. Initial studies were performed on 15 to 20 transgenic lines for each construct and additional studies were performed on three to four selected lines. Plants for additional studies were generated from fresh intermodal stem cuttings. Tissues collected were young leaf (leaf plastochron index, LPI-0 and 1), mature leaf (LPI-6), stem (internode portion between LPI 6 and 8) were collected, frozen in liquid nitrogen and stored at −80° C. until used.

RNA Extraction and Gene Expression Studies

RNA from the ground frozen stem samples was extracted using Plant RNA extraction kit (Sigma, St Louis, Mo.) with modifications. Briefly, 100 mg of frozen sample was extracted with 850 µl CTAB buffer maintained at 65° C. followed by chloroform:isoamylalcohol (24:1 v/v). After passing the supernatant through filtration column, the elutant was diluted with 500 µl of 95% EtOH and passed through the binding column. Further steps including on-column DNAse digestion were followed as per the manufactures protocol. cDNA was synthesized from 1.5 µg total RNA using oilgo dT primers and RevertAid Reverse Transcriptase (Thermofisher). Quantitative reverse transcriptase PCR (qRT-PCR) was performed in a 384 well plate using cDNA (3 ng), gene specific primers (250 nM, list provided in Supplemental file) and iTaq Universal SYBR Green Supermix (1×, Bio Rad). Gene expression was calculated using delta cT or delta-delta cT method using the expression of housekeeping genes 18S ribosomal RNA and Ubiquitin-conjugating enzyme E2 for template normalization (Gene accession numbers and primer sequence information can be found in Payyavula et al. 2014; Plant Biol. 2014 Oct. 7; 14:265. doi: 10.1186/s12870-014-0265-8).

Cellulose Content, Degree of Polymerization and Crystallinity

Cellulose was estimated from air-dried stem sample using anthrone method (Updegraff, 1969). Stem sample (25 mg) was first digested with 500 µl of acetic-nitric acid reagent (100 ml of 80% acetic acid mixed with 10 ml of nitric acid) at 98° C. for 30 min. After cooling, the sample was centrifuges, discarded the supernatant, and washed with water. After brief centrifugation, water was discarded and the pellet was digested with 67% (v/v) sulfuric acid for 1 hr at room temperature. An aliquot of the mix was diluted (1:10) with water. In a PCR tube, 10 µl of diluted reaction mix, 40 µl of water and 100 µl of freshly prepared anthrone reagent (0.5 mg anthrone $ml^{-1}$ of cold concentrated sulfuric acid) were added and heated for 10 min at 96° C. Samples were cooled and absorbance ($A_{630}$) was measured. Cellulose was then estimated based on the absorbance of glucose standards. Holocellulose and α-cellulose samples were prepared and employed in gel permeation chromatography (GPC) and For $^{13}$C-CPMAS NMR analysis of cellulose using established protocols.

Anatomy and Histological Analysis

Transgenic *Populus* stems were sampled internode number nine (counted in ascending order from stem apex towards base of stem). Freshly prepared hand sections were stained with phloroglucinol to gauge of the extent of red staining, which is indicative of lignin in cell walls in sample, under a dissection a simple microscope.

Stem Carbohydrate Composition Analysis

Roughly 25 mg air-dried stem sample was weighed in 2-ml tube, and extracted twice at 85° C. with a total of 2-ml ethanol (80%). The supernatant was collected in a new 2-ml tube and was reextracted with 50 mg activated charcoal (Sigma) to eliminate pigments that interfere with sugar analysis. A 1-ml aliquot of the pigment free extract was incubated over-night in a heating block maintained at 50° C., and the resulting pellet was dissolved in 120 µl water. A 10 µl aliquot was used for estimation of sucrose and glucose using kits (Sigma). Starch from the pellet was digested by 1 U of α-amylase (from *Aspergillus oryzae*, Sigma) and amyloglucosidase (from *Aspergillus niger*, Sigma). After starch removal, the pellet was dried over night at 95° C. and used for estimating structural sugars. Roughly, 5 mg sample was weighed in a 2-ml tube, digested with 50 µl of 75% v/v $H_2SO_4$ for 60 min. The reaction was diluted by adding 1.4 ml water. Tubes were sealed using lid-locks and were autoclaved for 60 min in liquid cycle. After cooling, the sample was neutralized with $CaCO_3$ and used for estimating sugar composition on high performance liquid chromatography (HPLC, LaChrom Elite® system, Hitachi High Technologies America, Inc.) as described previously.

Glucose Release and Ethanol Conversion

Separate hydrolysis and fermentation (SHF) was used to evaluate the digestibility of the biomass samples as described previously (Fu et at, 2011; Yee et at, 2012). Extract free biomass was autoclaved for sterilization purposes and the hydrolysis and fermentations were performed in biological triplicate at 5.0% (w/v) biomass loading in a total volume of 20 ml at a pH of 4.8 with a final concentration of 50 mM citrate buffer and 0.063 mg ml$^{-1}$ streptomycin. The hydrolysis was performed using the commercial hydrolytic enzyme blends (Novozymes, Wilmington, Del., USA). Cellic®-Ctec2 was loaded at 20 mg protein gram$^{-1}$ dry biomass, and Novozyme 188 and Cellic® Htec2 were loaded at 25% and 20% (v/v) of Ctec2, respectively. The biomass and enzymes were incubated at 50° C. and 120 rpm for 5 days. The hydrolysate was then fermented with *Saccharomyces cerevisiae* D5A (ATCC 200062) at 35° C. and 150 rpm with a final concentration of 0.5% (w/v) yeast extract. Hydrolysate and fermentation broth samples were analyzed for glucose and ethanol using HPLC equipped with a refractive index detector (model L-2490). The products were separated on Aminex® HPX-87H column (Bio-Rad Laboratories, Inc.), at a flow rate 0.5 ml min$^{-1}$ of 5.0 mM sulfuric acid and a column temperature of 60° C. and were quantified as described elsewhere.

Sugar Release Assay

In a 96-well solid Hastelloy microtiter plate, the dried soluble extract and starch-free sample (5.0±0.3 mg) and water (250 µl) were steam heated at 180° C. for 17.5 min in a Parr reactor after sealing and clamping. After cooling, 40 µl of buffer-enzyme stock (CTec2 (Novozymes, Franklinton, N.C.) in 1 M sodium citrate buffer) was added to achieve a final loading of 70 mg protein per g biomass, the plates were sealed with adhesive film and a magnetic clamping system (to maintain seal integrity) and incubated at 50° C. for 70 h. Samples were mixed and centrifuged at 1600 rpm for 15 min. The reactor plates were sampled with a Biomek FX 96-channel liquid handler (Beckman Coulter Inc., Indianapolis, Ind.). Twenty µl aliquots were diluted 1:20 (v:v) with 200 mM citrate buffer (pH 5.0) and analyzed for glucose and xylose concentration using the glucose oxidase- and xylose dehydrogenase-based assays (Megazyme, Bray, Ireland) as described previously.

Example 2: PdIQD1 was Identified as Uniquely Expressed in Xylem, Under Tension Stress and Co-Expression Analyses Using PdCesA A cross-cutting study was used to identify new cellulose biosynthesis pathway players in *Populus*, a model bioenergy plant, based on genetic and genomic approaches. Such an approach resulted in identification of several promising new candidate cellulose biosynthesis pathway genes. Here, evidence is provided that one particular candidate gene, Potri.001G375700, *Populus trichocapra* gene name; PoptrIQD1, *Populus deltoides* gene name; PdIQD1 (older gene designation referred to the locus as SF16), has a functional impact on cellulose biosynthesis, secondary wall formation, sugar release and biomass production in *Populus*.

Figure 2:
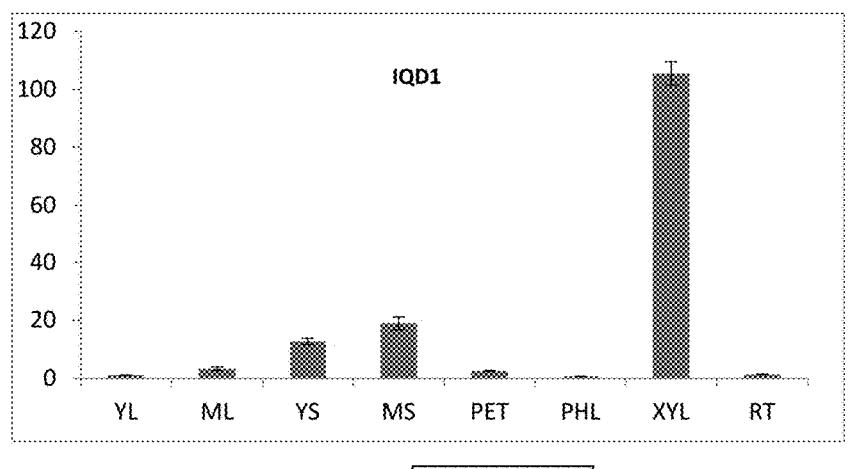
FIG. 2. Relative expression of PdIQD1 gene in various *Populus deltoides* tissue types. YL—young leaf, ML—mature leaf, YS youg stem, MS—mature stem, PET—petiole, PHL—phloem, XYL—xylem, and RT—root. Data represent means±SE (n=3).

PoptrIQD1 was identified as uniquely expressed in xylem based on the following experiments. 1) tension stress response profiling (a physiological response to bending/leaning in stems of angiosperms, where enhanced xylem cell proliferation and cellulose production in new cell wall layers [>90% cellulose] occurs) (FIG. 1), 2) xylem proteome profiling (a tissue type where enhanced cellulose and secondary cell wall production occurs) and 3) co-expression studies (using a cellulose synthase, PoptrCesA gene as a bait) identified PoptrIQD1 gene to be upregulated during enhanced cellulose biosynthesis phases. A qRT-PCR assay confirmed the enhanced expression of PdIQD1 gene in *Populus deltoides* xylem tissue (FIG. 2).

Example 3: PdIQD1 is a Canonical Calmodulin-Binding Protein IQ 67-Domain 1 Gene Closely Related to AtIQD10 and the Gene Family is Expanded in *Populus* Relative to *Arabidopsis*

Figure 11:
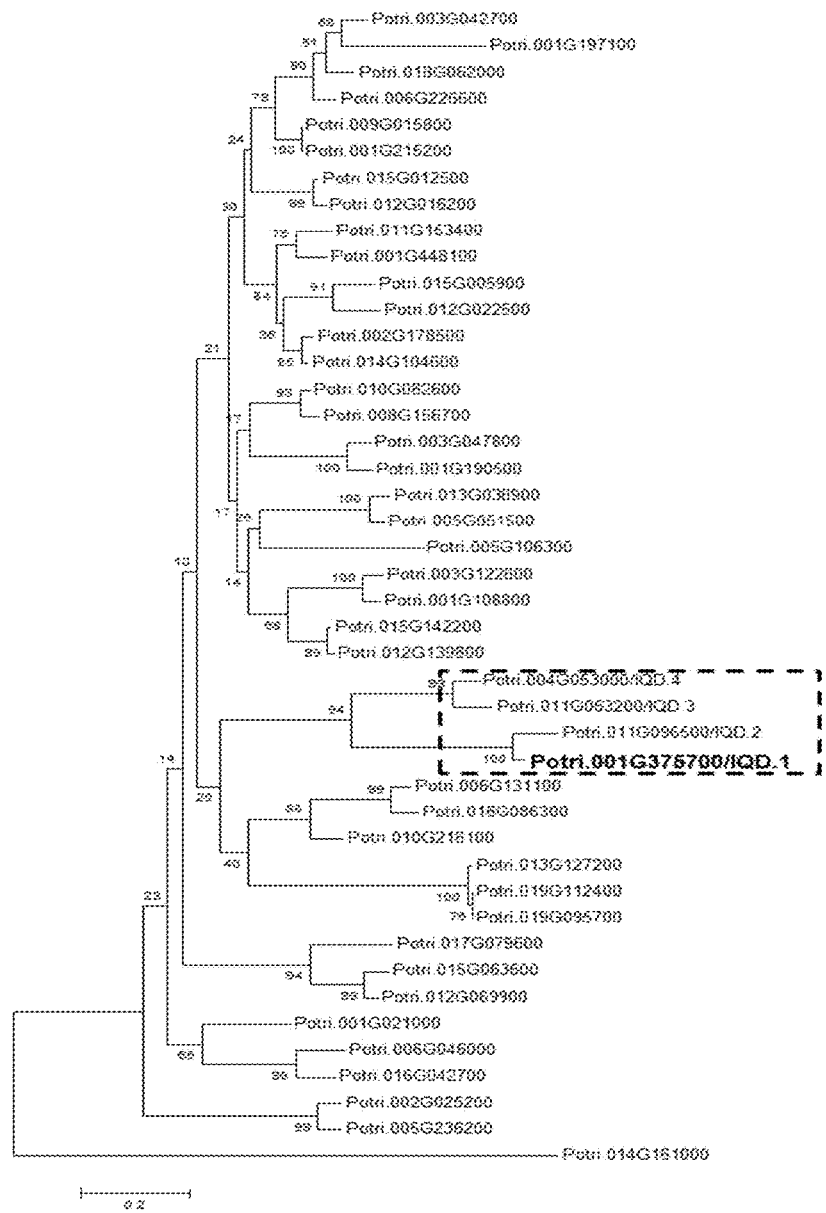
FIG. 11: Phylogenetic tree of predicted IQD protein sequences

Sequence analysis suggests that PdIQD1, codes for a calmodulin-binding protein belonging to the family IQD (named based on the IQ-amino acid rich region in the N-terminal of the predicted protein sequence). There are nearly 44 such IQD genes in the *Populus* genome v 3.0 (Phytozome.org). A phylogenetic tree of predicted IQD protein sequences was developed using neighbor joining method. The closely related IQD paralogs are shown in a box and the PoptrIQD1 or the corresponding *P. deltoides* ortholog, PdIQD1, highlighted in bold was the target in this study (FIG. 11).

The full-length protein sequence of PoptrIQD1 (Potri.001G375700) consists of 302 AA (SEQ. ID. NO: 2) and is as follows:

MGCLFSGNWLKSIIRTRKAKKDASKKVKVHSATEKANGSKESSPAHGESS

NLANGDLESNIHVAPGLSAEYIAAVRIQDAFRAYKARKAMHRLKGAVRFN

VLIHGHDTQKQASSTLSHIHSWSNIQAQIRARRHHMVTEGRIKQKKLENQ

LKLEARLQEIEVEWCGGSDTMEEILSRIQQREEAAVKRERAMAYAFSHQW

RANPTQYLGQAYYSLGKENWGWSWKERWIAARPWEIRVHAELHNLKKAHP

KQESKTTLPTKPALSNGKVTAKSKMLPSPAVDCQAAQVASSTAGSSHLLI

PS

Example 4: Generation of Transgenic PdIQD1 RNAi Plants

Figure 3:
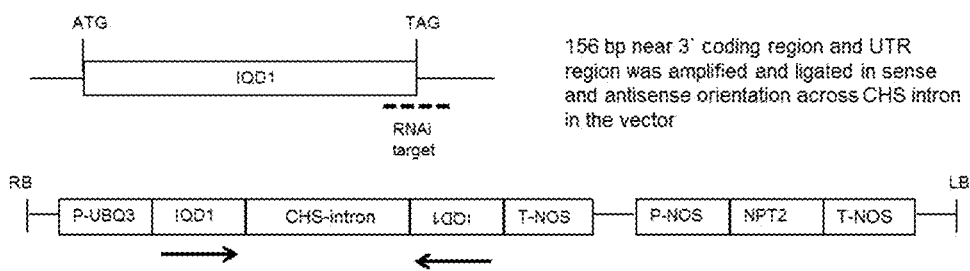
FIG. 3. Construct design used to develop the IQD1 gene-specific RNAi construct.

In order to evaluate the functional role of PoptrIQD1 or the corresponding PdIQD1 on plant cell wall and growth properties, stable transgenic *Populus deltoides* plants with downregulated PdIQD1 expression were generated. Stable down-regulation of PdIQD1 gene target was achieved using RNAi gene silencing technology in combination with *agrobacterium* mediated transformation of plant cells. Other alternate technologies for achieving RNA silencing include, but not limited to, antisense and artificial miRNA (amiRNA) technologies. The following was used to construct design to develop the IQD1 gene-specific RNAi construct. *Populus deltoides* xylem cDNA library was used as a template to generate the gene-specific construct based on PoptrIQD1 reference sequence for targeted down-regulated of PdIQD1 in *P. deltoides* (FIG. 3).

Potri.001G375700 (SEQ. ID NO: 1), Coding sequence (translated region) (SEQ, ID. NO: 3) from reference genome, *P. trichocarpa* nisquallyl):

```
CATGGGTTGTCTCTTCTCTGGGAACTGGTTGAAGTCAATTATAAGAACGA
GAAAGGCGAAGAAAGATGCATCAAAGAAAGTAAAGGTACACTCGGCTACC
GAAAAGGCAAACGGGTCAAAGGAGAGCTCACCCGCCCATGGAGAATCAAG
TAATCTTGCCAATGGTGATTTGGAGAGCAATATTCATGTTGCTCCTGGAT
TGTCTGCTGAATATATAGCTGCTGTCAGGATTCAAGATGCTTTTCGGGCA
TACAAGGCAAGAAAAGCAATGCACCGTCTTAAGGGCGCCGTGAGGTTCAA
TGTGCTGATTCATGGTCATGACACTCAAAAGCAAGCTTCAAGCACATTAA
GCCATATTCATTCATGGAGCAACATACAGGCACAGATTAGAGCCCGCCGG
CACCATATGGTCACCGAAGGCCGTATCAAGCAAAAGAAATTAGAAAACCA
GTTGAAACTCGAGGCCAGACTTCAAGAGATTGAGGTGGAGTGGTGCGGTG
GCTCCGATACCATGGAGGAAATCCTTTCCAGGATCCAGCAAAGAGAAGAA
GCAGCAGTAAAGCGTGAACGAGCCATGGCATATGCCTTCTCTCATCAGTG
GAGAGCCAACCCTACCCAATATCTAGGCCAGGCCTATTACAGCCTTGGCA
AAGAAAACTGGGGTTGGAGCTGGAAGGAGCGCTGGATTGCTGCTCGGCCA
TGGGAGATTAGGGTTCATGCTGAGCTTCATAACCTCAAGAAAGCTCATCC
AAAGCAAGAGAGCAAAACGACACTTCCAACCAAACCTGCTTTGTCAAATG
GGAAGGTGACTGCTAAATCTAAAATGTTGCCTAGCCCAGCTGTGGATTGT
CAAGCTGCCCAGGTTGCCAGTTCTACAGCCGGCTCGTCTCATCTGCTGAT
TCCAAGTTGA
```

The "IQD1" insert in the construct design above included the following target region (indicated within asterisks "* *") within the full-length coding sequence of the IQD1 gene (SEQ. ID. NO: 1). The underlined nucleotides indicate the translational start signal. The underlined, italicized nucleotides indicate the translational stop signal.

```
CCCCTTTCCACCTATTTCTTGCATTGCACTTCACCTTCTACTTCTTAATT
AATACTTGGAGTCCCAATATTGATCTCCACAACCCAATCCAACGAAGAAT
GTGTTGCTTCTCTCTTTGAACCCCCCATAAAAACAAACATGGGTTGTCTC
TTCTCTGGGAACTGGTTGAAGTCAATTATAAGAACGAGAAAGGCGAAGAA
AGATGCATCAAAGAAAGTAAAGGTACACTCGGCTACCGAAAAGGCAAACG
GGTCAAAGGAGAGCTCACCCGCCCATGGAGAATCAAGTAATCTTGCCAAT
GGTGATTTGGAGAGCAATATTCATGTTGCTCCTGGATTGTCTGCTGAATA
TATAGCTGCTGTCAGGATTCAAGATGCTTTTCGGGCATACAAGGCAAGAA
AAGCAATGCACCGTCTTAAGGGCGCCGTGAGGTTCAATGTGCTGATTCAT
GGTCATGACACTCAAAAGCAAGCTTCAAGCACATTAAGCCATATTCATTC
ATGGAGCAACATACAGGCACAGATTAGAGCCCGCCGGCACCATATGGTCA
CCGAAGGCCGTATCAAGCAAAAGAAATTAGAAAACCAGTTGAAACTCGAG
GCCAGACTTCAAGAGATTGAGGTGGAGTGGTGCGGTGGCTCCGATACCAT
GGAGGAAATCCTTTCCAGGATCCAGCAAAGAAGAAGCAGCAGTAAAGC
GTGAACGAGCCATGGCATATGCCTTCTCTCATCAGTGGAGAGCCAACCCT
ACCCAATATCTAGGCCAGGCCTATTACAGCCTTGGCAAAGAAAACTGGGG
TTGGAGCTGGAAGGAGCGCTGGATTGCTGCTCGGCCATGGGAGATTAGGG
TTCATGCTGAGCTTCATAACCTCAAGAAAGCTCATCCAAAGCAAGAGAGC
AAAACGACACTTCCAACCAAACCTGCTTTGTCAAATGGGAAGGTGACTGC
TAAATCTAAAATGTTGCCTAGCCCA*GCTGTGGATTGTCAAGCTGCCCAG
GTTGCCAGTTCTACAGCCGGCTCGTCTCATCTGCTGATTCCAAGT*TGA*CC
TTCGTGATGCTCCCTTCTTGATCCTGTGTCTCTGTATTGTTTATTTTCGG
GGTTGGTGTGAGATTGGCATGCAGCGTGTAAA*ATAAACATATTTTTGCT
TACAGTTATTATTAAGTAAATTATCTTAGTAACTAAAAAGATTCATCGAG
CAAATTTGGCTTGTTCGGTAATGACAAGAGGCTTCATTTTCTTGCCTCGA
AAAGAAGTAACATGGGCATGGAGCTCGAAACCACCGAGGAAGGATGCATT
TTAACCGTGAAATTAATTAATGTTCTTAAATCAGCAGGCAACTAGAAGAC
CTTCGCACTTTGAGCTAGCTCCTGTGTTCATTATGCATCAATTACCACAC
CAATCCATTGTTAGTTGTATAGCTAGACAAGAACAAGTACATCCCAACAA
GATCTTGCATTCCTAACCCCAATAAATCAGTATTTTCTTGTAAATCTTA
GTTTACTAAGGCGCTATTCAGCATGTTCATCTCATGCGTACCGGTATCCA
CCCCAGCCACCCTATGTTATTAGCTTTCAACGAGGTAAAAGAAGGGAATT
TGGTGTAGAATTACGCTTATGGCTGTACCTTGCCTTTGCAGTAGTAATTA
TCAACTCCAGTATAAAGAACACTAGCTAGTAACCAGCAGAAAGCAAAATG
TCACCATCTCCATTGAATCCAAGTGTTTCACTTTAATATATTTTGGTTTT
TCCCCGGGTGCCAAAAAAAAAACCCAGCTAGGCTGAAGAGATTTTTTTGA
GGGACTGAGATTTACAGGGTAGGGGACCGAAGACAGATGGCAAAGTATCG
CATTTTTAGTGGTATCCATCTGTGTATTCTTCCATAATTGTGCCTTGCTG
TGTTCATGCCATTATGTGTATTCTTCCATAATTGAGCTTTGCTGTGTTCA
TCCCATTATTTAATAGTGT
```

Figure 4:
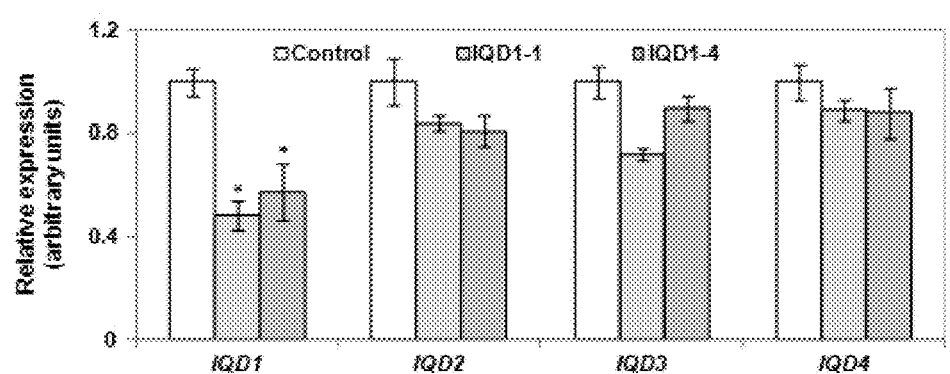
FIG. 4. Sequence-specific down-regulation of the target gene PdIQD1.

The sequence-specific down-regulation of the one target gene IQD1 (PdIQD1) was verified by studying the relative expression (arbitrary units) of three other paralogous genes closely related to PdIQD1 (PdIQD2-4) in control and IQD1 transgenic lines. Our assays confirmed that while downregulation in expression level of the target gene was confirmed (FIG. 4), the expression of other PdIQD genes was not significantly altered in two independent IQD1 transgenic RNAi lines, IQD1-1 and IQD1-4. This provides evidence that the observed transgenic phenotype is due to the downregulation of expression of PdIQD1 only.

Figure 5A:
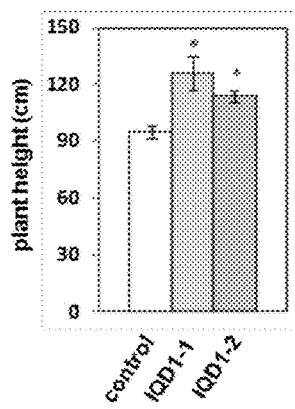
FIG. 5A. Plant height of PdIQD1 RNAi lines.
Figure 5B:
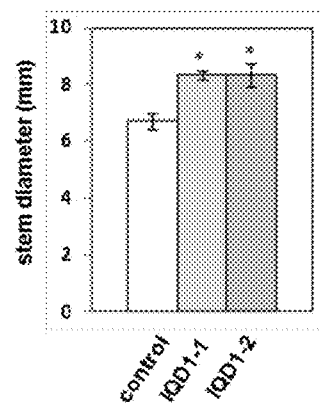
FIG. 5B. Stein diameter of PdIQD1 RNAi lines.
Figure 5C:
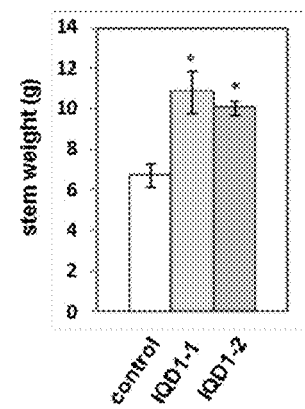
FIG. 5C. Stem weight of PdIQD1 RNAi lines.

Example 5: Greenhouse-Grown PoptrIQD1 Transgenic RNAi Plants Showed Increased Plant Growth and Stem Biomass Formation Characterization of PCR- and RT-PCR-confirmed PdIQD1 RNAi plants was undertaken at cell, organ and whole plant levels in controlled greenhouse conditions. A minimum of ten lines were employed in preliminary phenotyping efforts for PdIQD1 lines and two selected lines were included in deeper characterization studies. These independent lines or transformation events are represented here as IQD1-1 and IQD1-2, which include three biological replicates or ramets each. PdIQD1 RNAi lines had significantly greater plant height (FIG. 5A), stem diameter (FIG. 5B) and stem dry weight (FIG. 5C) as compared to the control (empty vector transformation control).

Figure 6:
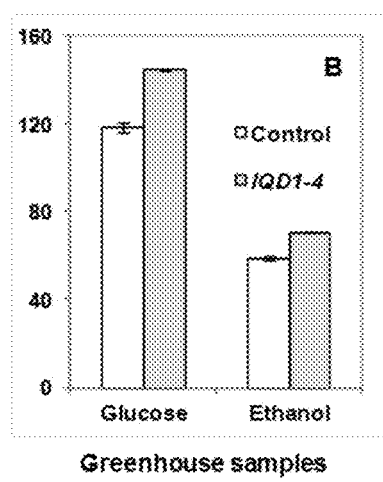
FIG. 6. Glucose release and ethanol conversion efficiency of PdIQD plants.

Example 6: Greenhouse-Grown PdIQD1 Transgenic RNAi Plants Showed Lower Recalcitrance and Better Sugar Release Properties Analysis of sugar release efficiency of debarked, dried and ground stem samples from control and transgenic plants showed that the modified PdIQD gene expression resulted in stems with reduced recalcitrance and improved ethanol conversion. The PdIQD plants had ~20% higher glucose release and ethanol conversion efficiency as compared to control plants (FIG. 6).

Figure 7A:
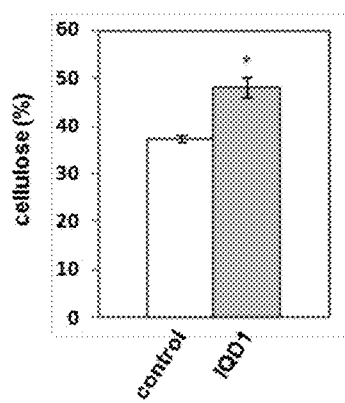
FIG. 7A. Cellulose content in cell walls.
Figure 7B:
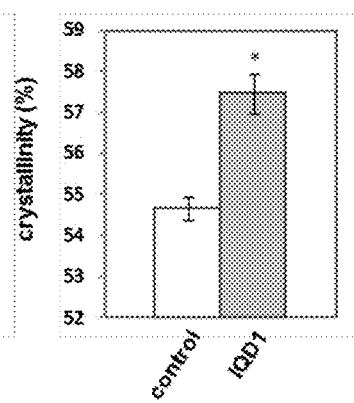
FIG. 7B. Crystallinity of cellulose in cell walls.
Figure 7C:
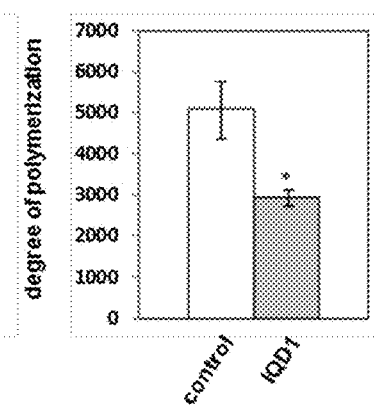
FIG. 7C. Cellulose polymerization in cell walls.

Example 7: PdIQD1 RNAi Plants Showed Altered Cell Wall Composition with Higher Cellulose Content Wet chemistry-based quantification of cellulose content showed that the percentage of cellulose (useable substrate for cellulosic fuels) is higher in the transgenic stem cell walls (FIG. 7A). NMR techniques showed that the crystallinity of cellulose is higher in the cell walls (FIG. 7B), while the degree of polymerization is lower (FIG. 7C).

Example 8: PdIQD1 Silencing Resulted in Increased Xylem Growth

Figure 8:
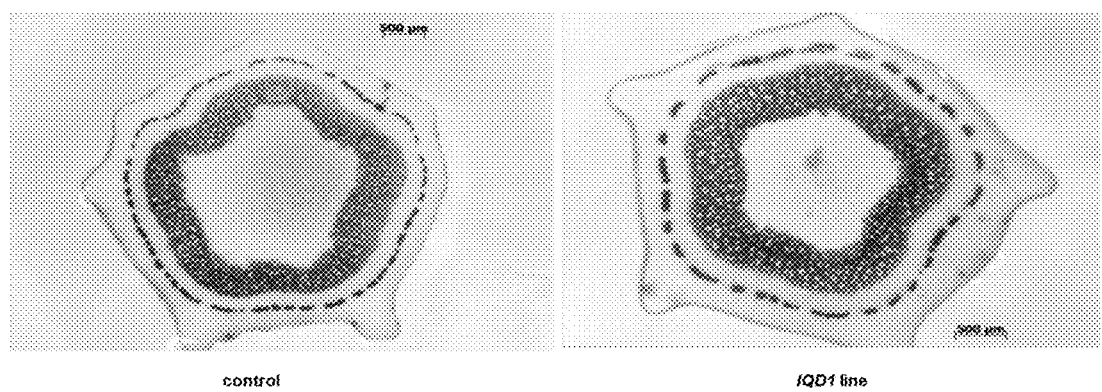
FIG. 8. Increase in xylem growth for PdIQD1 silencing.

In order to understand the anatomical changes that underlie the morphometric trait of increased stem diameter in transgenic plants, anatomical observation of stem crosssections from internode number 9 was undertaken. The results show that there are a greater number of secondary walled cells, where the average vessel size is larger, in transgenic plants relative to the control (FIG. 8).

Example 9: PdIQD1 Potentially Participates in the Cell Wall and Biomass Formation Signaling Pathways Subcellular protein localization and protein interaction experiments were undertaken to shed light on the molecular mechanism of action of PdIQD1 in impacting biomass properties of *Populus*.

Protein localization experiments showed that IQD1 localizes in two subcellular compartments. The protein was found to strongly localize in the nuclear compartment and to a weaker extent in the plasma membrane region.

It was verified that PdIQD1 protein interacts with a Kinesin Light Chain-related protein-1 (KLCR-1) in vivo. A positive green fluorescence signal was observed from nuclear compartment upon introduction of PdIQD1 and PdKLCR-1 split-GFP constructs in live *Populus* protoplasts. The interaction between PdIQD1 and PdKLCR-1 was also confirmed by yeast two hybrid assays. Additional yeast two hybrid screening assays have been designed to explore interaction with calmodulin protein and known cellulose pathway factors. A positive green fluorescence signal was observed from the nucleus upon in vivo interaction of tagged PdIQD1/IQD1 protein with tagged KCLR-1 protein.

Figure 9:
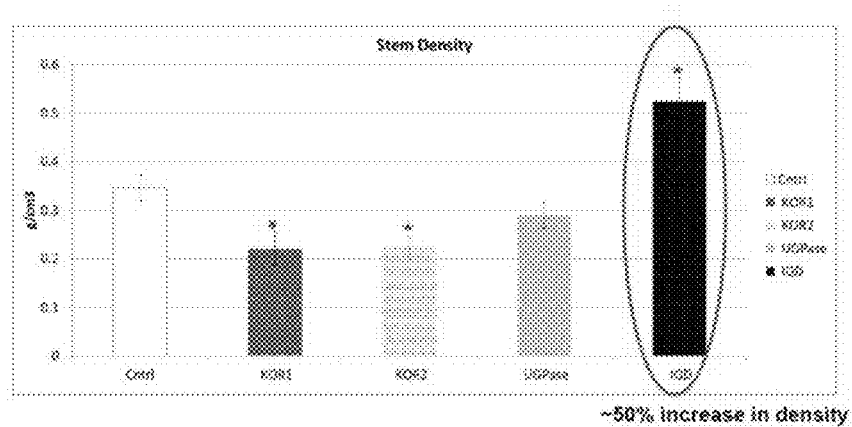
FIG. 9. Stem density of PdIQD1 RNAi stem samples.
Figure 10:
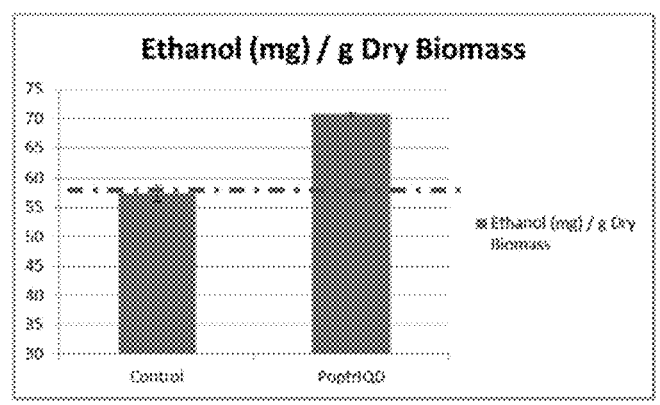
FIG. 10. Ethanol production of PdIQD1 RNAi stem samples.

Example 10: PoptrIQD1 RNAi Plants Perform Better than Control Plants in the Field in Terms of Stem Density and Ethanol Production In order to evaluate the stability of favorable biomass traits observed in controlled greenhouse conditions, stem samples collected from transgenic and controls lines growing under variable abiotic and biotic variables in the field settings (stool bed for maintaining transgenic collection) were studied. The transgenic PdIQD1 RNAi stem samples had significantly higher stem density (up to 50% increase in one line) relative to control (FIG. 9) and enhanced ethanol production per unit dry biomass (FIG. 10) compared to control. These lines of experimental evidences strongly suggest a key functional for PdIQD1 in determining cellulose, cell wall, biomass and growth properties of *Populus* plants.

---

What is claimed is:

1. A method for increasing biomass, cellulose content or sugar release in a *Populus* plant, the method comprising:
   (i) transforming *Populus* plants with a recombinant binary vector comprising a DNA expression construct, wherein the DNA expression construct comprises a heterologous promoter operably linked to a first DNA segment of 100-500 nucleotides long that corresponds to at least a portion of the 3' UTR region of the IQD1 gene as set forth in SEQ ID NO: 1, a spacer segment and a second DNA segment that is fully complementary to the first DNA segment, wherein the first and second DNA segments are arranged in a 5' to 3' direction, respectively, in the DNA expression construct;
   (ii) expressing said DNA construct to produce double stranded with hairpin loop RNAi inhibitory molecule in said transformed *Populus* plants, and wherein expression of endogenous IQD1 gene and its encoded IQD1 protein in said *Populus* plants is reduced; and
   (iii) selecting a transformed *Populus* plant from transformed *Populus* plants of step (ii) which expresses said RNAi inhibitory molecule and exhibits increase in biomass, cellulose content or sugar release as compared to a wild-type untransformed *Populus* plant species lacking said DNA expression construct.

2. The method according to claim 1, wherein said biomass is increased in said selected transformed plant.

3. The method according to claim 1, wherein said cellulose content is increased in said selected transformed plant.

4. The method according to claim 1, wherein said sugar release is increased in said selected transformed plant.

* * * * *